US009381506B2

(12) United States Patent
Diao et al.

(10) Patent No.: US 9,381,506 B2
(45) Date of Patent: Jul. 5, 2016

(54) COBALT CATALYSTS AND THEIR USE FOR HYDROSILYLATION AND DEHYDROGENATIVE SILYLATION

(71) Applicants: Tianning Diao, New York, NY (US); Paul J. Chirik, Princeton, NJ (US); Aroop Kumar Roy, Mechanicville, NY (US); Kenrick Lewis, Flushing, NY (US); Keith J. Weller, Rensselaer, NY (US); Johannes G. P. Delis, Bergen op Zoom (NL); Renyuan Yu, Beijing (CN)

(72) Inventors: Tianning Diao, New York, NY (US); Paul J. Chirik, Princeton, NJ (US); Aroop Kumar Roy, Mechanicville, NY (US); Kenrick Lewis, Flushing, NY (US); Keith J. Weller, Rensselaer, NY (US); Johannes G. P. Delis, Bergen op Zoom (NL); Renyuan Yu, Beijing (CN)

(73) Assignees: Momentive Performance Materials Inc., Waterford, NY (US); Princeton University, Princeton, NJ (US)

(*) Notice: Subject to any disclaimer, the term of this patent is extended or adjusted under 35 U.S.C. 154(b) by 0 days.

(21) Appl. No.: 14/547,726

(22) Filed: Nov. 19, 2014

(65) Prior Publication Data
US 2015/0141648 A1    May 21, 2015

Related U.S. Application Data

(60) Provisional application No. 61/906,204, filed on Nov. 19, 2013, provisional application No. 62/031,463, filed on Jul. 31, 2014.

(51) Int. Cl.
| | |
|---|---|
| *C07F 15/06* | (2006.01) |
| *C08G 77/08* | (2006.01) |
| *C07F 7/08* | (2006.01) |
| *B01J 31/22* | (2006.01) |
| *C07F 19/00* | (2006.01) |
| *C07F 7/18* | (2006.01) |

(52) U.S. Cl.
CPC ........... *B01J 31/2295* (2013.01); *C07F 7/0856* (2013.01); *C07F 7/0879* (2013.01); *C07F 7/184* (2013.01); *C07F 7/1876* (2013.01); *C07F 15/06* (2013.01); *C07F 19/00* (2013.01); *B01J 2231/14* (2013.01); *B01J 2231/323* (2013.01); *B01J 2531/845* (2013.01)

(58) Field of Classification Search
USPC ......................................... 546/14, 2; 528/14
See application file for complete search history.

(56) References Cited

U.S. PATENT DOCUMENTS

| | | |
|---|---|---|
| 3,159,601 A | 12/1964 | Ashby et al. |
| 3,220,972 A | 11/1965 | Lamoreaux |
| 3,296,291 A | 1/1967 | Chalk et al. |
| 3,775,452 A | 11/1973 | Karstedt |
| 3,928,629 A | 12/1975 | Chandra et al. |
| 4,550,152 A | 10/1985 | Faltynek |
| 4,572,791 A | 2/1986 | Onopchenko et al. |
| 4,578,497 A | 3/1986 | Onopchenko et al. |
| 4,729,821 A | 3/1988 | Timmons et al. |
| 4,788,312 A | 11/1988 | Paciorek et al. |
| 5,026,893 A | 6/1991 | Paciorek |
| 5,166,298 A | 11/1992 | Friedman et al. |
| 5,331,075 A | 7/1994 | Sumpter et al. |
| 5,432,140 A | 7/1995 | Sumpter et al. |
| 5,866,663 A | 2/1999 | Brookhart et al. |
| 5,955,555 A | 9/1999 | Bennett |
| 6,103,946 A | 8/2000 | Brookhart et al. |
| 6,214,761 B1 | 4/2001 | Bennett |
| 6,265,497 B1 | 7/2001 | Herzig |
| 6,278,011 B1 | 8/2001 | Chen et al. |
| 6,281,303 B1 | 8/2001 | Lavoie et al. |
| 6,297,338 B1 | 10/2001 | Cotts et al. |
| 6,417,305 B2 | 7/2002 | Bennett |
| 6,423,848 B2 | 7/2002 | Bennett |
| 6,432,862 B1 | 8/2002 | Bennett |
| 6,451,939 B1 | 9/2002 | Britovsek |
| 6,455,660 B1 | 9/2002 | Clutton et al. |
| 6,458,739 B1 | 10/2002 | Kimberley et al. |
| 6,458,905 B1 | 10/2002 | Schmidt et al. |
| 6,461,994 B1 | 10/2002 | Gibson et al. |
| 6,472,341 B1 | 10/2002 | Kimberley et al. |
| 6,620,895 B1 | 9/2003 | Cotts et al. |
| 6,657,026 B1 | 12/2003 | Kimberley et al. |
| 7,053,020 B2 | 5/2006 | DeBoer et al. |
| 7,148,304 B2 | 12/2006 | Kimberley et al. |
| 7,161,005 B2 | 1/2007 | Schlingloff et al. |
| 7,247,687 B2 | 7/2007 | Cherkasov et al. |
| 7,268,096 B2 | 9/2007 | Small et al. |
| 7,429,672 B2 | 9/2008 | Lewis et al. |
| 7,442,819 B2 | 10/2008 | Ionkin et al. |
| 7,456,285 B2 | 11/2008 | Schlingloff et al. |
| 7,696,269 B2 | 4/2010 | Cruse et al. |

(Continued)

FOREIGN PATENT DOCUMENTS

| | | |
|---|---|---|
| CN | 1727349 | 2/2006 |
| EP | 0786463 | 7/1997 |

(Continued)

OTHER PUBLICATIONS

Zhu, D. et al.: A measure for donor and acceptor properties of diiminepyridine-type ligands. Organometallics, vol. 27, pp. 2699-2705, 2008.*

(Continued)

*Primary Examiner* — Charanjit Aulakh
(74) *Attorney, Agent, or Firm* — Joseph E. Waters; McDonald Hopkins LLC

(57) ABSTRACT

Disclosed herein are cobalt terpyridine complexes containing a single ligand coordinated to the cobalt, and their use as hydrosilylation and/or dehydrogenative silylation and crosslinking catalysts. The cobalt complexes also exhibit adequate air stability for handling and manipulation.

26 Claims, No Drawings

(56) References Cited

U.S. PATENT DOCUMENTS

| | | |
|---|---|---|
| 8,236,915 B2 | 8/2012 | Delis et al. |
| 8,415,443 B2 | 4/2013 | Delis et al. |
| 2002/0058584 A1 | 5/2002 | Bennett |
| 2006/0263675 A1 | 11/2006 | Adzic et al. |
| 2007/0264189 A1 | 11/2007 | Adzic et al. |
| 2008/0262225 A1 | 10/2008 | Schlingloff et al. |
| 2008/0293878 A1 | 11/2008 | Funk et al. |
| 2009/0068282 A1 | 3/2009 | Schlingloff et al. |
| 2009/0296195 A1 | 12/2009 | Fontana et al. |
| 2011/0009565 A1 | 1/2011 | Delis et al. |
| 2011/0009573 A1 | 1/2011 | Delis et al. |
| 2012/0130021 A1 | 5/2012 | Tondreau et al. |
| 2012/0130105 A1 | 5/2012 | Lewis et al. |
| 2012/0130106 A1 | 5/2012 | Lewis et al. |
| 2013/0158281 A1 | 6/2013 | Weller et al. |
| 2014/0051822 A1 | 2/2014 | Atienza et al. |
| 2014/0243486 A1 | 8/2014 | Roy et al. |
| 2014/0330024 A1 | 11/2014 | Atienza et al. |
| 2014/0330036 A1 | 11/2014 | Lewis et al. |
| 2014/0343311 A1 | 11/2014 | Boyer et al. |
| 2015/0080536 A1 | 3/2015 | Diao et al. |
| 2015/0137033 A1 | 5/2015 | Diao et al. |

FOREIGN PATENT DOCUMENTS

| | | |
|---|---|---|
| GB | 2013207 | 8/1979 |
| TW | 200902541 | 1/2009 |
| WO | 9210544 | 6/1992 |
| WO | 02088289 | 11/2002 |
| WO | 03042131 | 5/2003 |
| WO | 2008085453 | 7/2008 |
| WO | 2011006044 | 1/2011 |
| WO | 2012/007139 | 1/2012 |
| WO | 2012071359 | 5/2012 |
| WO | 2013/043783 | 3/2013 |
| WO | 2013043846 | 3/2013 |
| WO | 2015023328 | 2/2015 |

OTHER PUBLICATIONS

Archer et al., "Arene Coordination in Bis(imino)pyridine Iron Complexes: Identification of Catalyst Deactivation Pathways in Iron-Catalyzed Hydrogenation and Hydrosilation," Organometallics, vol. 25, pp. 4269-4278 (2006).

Bowman et al., "Reduced N-Alkyl Substituted Bis(imino)pyridine Cobalt Complexes: Molecular and Electronic Structures for Compounds Varying by Three Oxidation States," Inorg. Chem. 2010, 49, 6110-6123, Germany.

Zhu et al., "A Measure for *-Donor and *-Acceptor Properties of Diiminepyridine-Type Ligands," Organometallics 2008, 27, 2699-2705.

Yeung, et al., "Cobalt and iron complexes of chiral C1- and C2-terpyridines: Synthesis, characterizationa dn use in catalytic asymmetric cyclopropanation of styrenes." Inorganica Chimica Acta 362 (2009) 3267-3273.

Bart et al., "Electronic Structure of Bis(imino)pyridine Iron Dichloride, Monochloride, and Neutral Ligand Complexes: A Combined Structural, Spectroscopic, and Computational Study," J. Am. Chem. Soc. 2006, 128, 13901-13912.

Bart et al., "Preparation and Molecular and Electronic Structures of Iron(0) Dinitrogen and Silane Complexes and Their Application to Catalytic Hydrogenation and Hydrosilation," Journal of the American Chemical Society, vol. 126, pp. 13794-13807 (2004).

Connelly et al., "Chemical Redox Agents for Organometallic Chemistry," Chem. Rev. 1996, 96, 877-910.

Atienza et al. "Synthesis, Electronic Structure, and Ethylene Polymerization Activity of Bis(imino)pyridine Cobalt Alkyl Cations," Agnewandte Chem. Int. Ed. 2011, 50, 8143-8147.

Glatz et al., "Terpyridine-Based Silica Supports Prepared by Ring-Opening Metathesis Polymerization for the Selective Extraction of Noble Metals," Journal of Chromatography A, vol. 1015, pp. 65-71 (2003).

Nagashima et al., "Dehydrogenative Silylation of Ketones with a Bifunctional Organosilane by Rhodium-Pybox Catalysts," Chem. Soc. of Jpn., Chemistry Letters, 1993, 347-350, Toyohashi, Aichi 441.

Hosokawa et al., "A Chiral Iron Complex Containing a Bis(oxazolinyl)phenyl Ligand: Preparation and Asymmetric Hydrosilylation of Ketones," Organometallics, 29, 5773-5775 (2010).

Kaul et al., "Immobilization of Bis(imino)pyridyliron (II) complexes on Silica," Organometallics, 2002, 21(1), 74-83.

Kim et al., "2,2':6',2"-Terpyridine and Bis(2,2':6',2"-terpyridine)Ruthenium(II) Complex on the Dendritic Periphery," Journal of Organometallic Chemistry, vol. 673, pp. 77-83 (2003).

Kroll et al., "Access to Heterogeneous Atom-Transfer Radical Polymerization (ATRP) Catalysts Based on Dipyridylamine and Terpyridine via Ring-Opening Metathesis Polymerization (ROMP)," Macromolecular Chemistry and Physics, vol. 202, pp. 645-653 (2001).

Field et al., "One-Pot Tandem Hydroamination/Hydrosilation Catalyzed by Cationic Indium(I) Complexes," Organometallics, vol. 22, pp. 4393-4395, Sep. 25, 2003.

Dekamin et al., "Organocatalytic, rapid and facile cyclotrimerization of isocyanates using tetrabutylammonium phthalimide-N-oxyl and tetraethylammonium 2-(carbamoyl) benzoate under solvent-free conditions," Catalysis Communications 12 (2010) 226-230.

Nesmeyanov et al., "Addition, Substitution, and Telomerization Reactions of Olefins in the Presence of Metal Carbonyls or Colloidal Iron," Tetrahedron, vol. 17, pp. 61-68 (1962).

Pal, et al., "Preparation and hydrosilylation activity of a molybdenum carbonyl complex that features a pentadentate bis (amino)pyridine lignad," Inorg Chem. Sep. 2, 2014; 53(17):9357-65. doi: 10.1021/ic501465v. Epub Aug. 20, 2014.

Jairam et al., "Ester Hydrolysis with 2,6-di(pyrazol-3-yl)pyridines and their Co 11 Complexes in Homogeneous and Micellar Media," Journal of Inorganic Biochemistry 84, 2001, 113-118, Toronto, Ontario, Canada.

Buschbeck et al., "Triethylene Glycol Ether End-grafted Carbosilane Dendrimers: Synthesis and Complexation Behavior," Inorganic Chemistry Communications, vol. 7, pp. 1213-1216, Oct. 13, 2004.

Seckin, "Preparation and Catalytic Properties of a Ru(II) Coordinated Polyimide Supported by a Ligand Containing Terpyridine Units," Journal of Inorganic and Organometallic Polymers and Materials, Apr. 9, 2009, 19(2), 143-151.

Sieh et al., "Metal-Ligand Electron Transfer in 4d and 5d Group 9 Transition Metal Complexes with Pyridine, Diimine Ligands," Eur. J. Inorg. Chem., 2012:444-462. doi 10.1002/ejic.201101072.

Speier et al., "The Addition of Silicon Hydrides to Olefinic Double Bonds. Part II. The Use of Group VIII Metal Catalysts," Journal of the American Chemical Society, vol. 79, pp. 974-979 (1956).

Thammavongsy et al., Ligand-Based Reduction of CO2 and Release of CO and Iron(II). Inorg. Chem., 2012, 51 (17), pp. 9168-9170. DOI: 10:1021/ic3015404. Publication Date (Web): Aug. 20, 2012.

Timpa, "Non-Innocent Pyridine Based Pincer Ligands and Their Role Catalysis" Nov. 1, 2010.

Tondreau, et al., "Enantiopure Pyridine Bis(oxazoline) "Pybox" and Bis(oxazoline) "Box" iron Dialkyl Complexes: Comparison to Bis(imino)pyridine Compounds and Application to Catalytic Hydrosilylation of Ketones," Organometallics, Jun. 9, 2009, 28(13), 3928-3940.

Tondreau, et al "Synthesis and electronic structure of cationic, neutral, and anionic bis (imino)pyridine iron alkyl complexes: evaluation of redox activity in single-component ethylene polymerization catalysts." J Am Chem Soc. Oct. 27, 2010; 132(42): 15046-59. doi: 10.1021/ja106575b.

Gibson et al., "The nature of the active species in bis(imino)pyridyl cobalt ethylene polymerisation catalysts," Chem. Commun., 2001, 2252-2253.

Wile, et al. "Reduction chemistry of aryl- and alkyl-substituted bis(imino)pyridine iron dihalide compounds: molecular and electronic structures of [(PDI)2Fe] derivatives." Inorg Chem May 4, 2009; 48(9):4190-200.

(56) References Cited

OTHER PUBLICATIONS

Tondreau, et al., "Iron Catalysts for Selective Anti-Markovnikov Alkene Hydrosilylation Using Tertiary Silanes," Science, vol. 335, No. 6068, Feb. 2, 2012. pp. 567-570.
Abu-Surrah et al., "New bis(imino)pyridine-iron(II)- and cobalt(II)-based catalysts: synthesis, characterization and activity towards polymerization of ethylene" Journal of Organometallic Chemistry 648 (2002) 55-61.
Albon et al., "Metal Carbonyl Complexes Involving 2,6Bix[I-(phenylimino)ethyl]pyridine; Bidentate Corrdination of a Potentially Tridentate Ligand" Inorganica Chimica Acta, 159 (1989) 19-22.
Alyea et al., "Terdentate NNN Donor Ligands Derived from 2,6-Diacetylpyridine" Syn. React. Inorg. Metal-Org. Chem., 4(6), 535-544 (1974).
Bouwkamp, "Iron-Catalyzed [$2\pi+2\pi$] Cycloaddition of $\alpha,\omega$-Dienes the Importance of Redox-Active Supporting Ligands" Journal of the American Chemical Society, 2006, V128 N41, p. 13340-13341.
Britovsek et al., "Novel Olefin Polymerization Catalysts Based on Iron and Cobalt," Chem. Commun., 1998, 849-850.
Cetinkaya et al., "Ruthenium(ii) complexes with 2,6-pyridyl-diimine ligands: synthesis, characterization and catalytic activity in epoxidation reactions" Journal of Molecular Catalysis A: Chemical 142 (1999) 101-112.
Corey et al., "Reactions of Hydrosilanes with Transition-Metal Complexes: Formation of Stable Transition-Metal Silyl Compounds," Journal of Chemical Reviews, vol. 99, pp. 175-292 (1999).
Haarman et al., "Reactions of [RhCl(diene)]2 with Bi- and Terdentate Nitrogen Ligands. X-ray Structures of Five-Coordinate Complexes," Am. Chem. Soc., Organometallics 1997, 16, 54-67.
Kickelbick et al., New J. Chem., 2002, 26, 462-468.
Kooistra et al., Inorganica Chimica Acta 357 (2004) 2945-2952.
Lapointe, et al., "Mechanistic Studies of Palladium(II)-Catalyzed Hydrosiliation and Dehydrogenative Silation Reactions," J. Amer. Chem. Soc. 119 (1997), pp. 906-917.
Lewis et al., "Hydrosilylation Catalized by Metal Colloids: A Relative Activity Study," Organometallics, 9 (1990), 621-625.
Lions et al., J. Chem. Soc. (A) 1957, vol. 79, 2733-2738.
Lu et al., "The Molecular Structure of a Complex of a 2,6-Diimino-Pyridine as a Bidentate Liandd with Molybdenum Carbonyl" Inorganica Chimica Acta, 134 (1987) 229-232.
Pangborn et al., "Safe and Convenient Procedure for Solvent Purification," Oraganometallics, 15:1518 (1996).
Randolph, Claudia L. et al., "Photochemical Reactions of ($\eta$5-Pentamethylcyclopentadienyl)dicarbonyliron-Alkyl and Silyl Complexes: Reversible Ethylene Insertion into an Iron-Silicon Bond and Implications for the Mechanism of Transition-Metal-Catalyzed Hydrosilation of Alkenes," Journal of the American Chemical Society, vol. 108, pp. 3366-3374 (1986).
Russell et al., "Synthesis of Aryl-Substituted Bis(imino)pyridine Iron Dinitrogen Complexes," Inorg. Chem. 2010, 49, 2782-2792.
Sacconi et al., "High-spin Five-Co-Ordinate Nickel (II) and Cobald (II) Complexes with 2,6-Diacetylepyridinebis (imines)," J. Chem. Soc. (A), 1968, 1510-1515.
Tondreau et al., "Bis(imino)pyridine Iron Complexes for Aldehyde and Ketone Hydrosilylation," Am. Chem. Soc., 2008, vol. 10, No. 13, 2789-2792.
Toma et al., J. Braz. Chem. Soc., vol. 7, No. 6, 391-394, 1996.
Suzuki, et al., "Random and block copolymerizations of norbornene with conjugated 1,3-dienes catalyzed by novel No compounds involving N- or O-donated ligands" Reactive & Functional Polymers 59 (2004) 253-266, May 6, 2004.
Seki et al., "Single-Operation Synthesis of Vinyl silanes from Alkenes and Hydrosilanes with the Aid of Ru (CO)12," Am. Chem. Soc., J. Org. Chem. 1986, 51, 3890-3895, Osaka, Japan.
Oro et al. "Hydrosilylation of Alkenese by Iridium Complexes," J. Mol. Catalysis, 1986, 37, 151-156.
Naumov et al., "Selective Dehydrogentative Silylation-Hydrogenation Reaction of Divinyldisiloxane with Hydrosilane Catalyzed by an Iron Complex," Journal of the American Chemical Society, 2012, vol. 134, Issue 2, 804-807, Osaka, Japan.
McAtee et al., "Preparation of Allyl and Vinyl Silanes by the Palladium-Catalyzed Silylation of Terminal Olefins: A Silyl-Heck Reaction**," Angewandte Chemie, Int. Ed. 2012, 51, 3663-3667.
Marciniec et al., "Competitve silylation of olefins with vinylsilanes and hydrosilanes photocatalyzed by iron carbonyl complexes," Inorg. Chem. Commun. 2000, 3, 371.
Lu et al., "Iridium-Catalyzed (Z)-Trialkylsilylation of Terminal Olefins," J. Org. Chem, 2010, 75, 1701-1705, Dallas, Texas.
Kuo, et al., "Electrochemical studies of nickel bis(2,2':6',2"-terpyridine) with alkyl/aryl/allyl bromides and activeated olefins in nonaqueous solvents" Jiemian Kexue Huishi, vol. 15, Issue 1, pp. 23-42, Journal, 1992, Coden: CMKCEW, ISSN: 1026-325X.
Kakiuchi et al., "Dehydrogenative Silylation of 1,5-Dienes with Hydrosilanes Catalyzed by RhCl (PPh3)3," Am. Chem. Soc., Organometallics, 1993, 12, 4748-4750, Kagawa, Japan.
Kakiuchi et al., "Completely Selective Synthesis of (E)-B-(triethylsilyl)styrenes by Fe3(CO)12-catalyzed Reaction of Styrenes With Triethylsilane," Journal of Organometallic Chemistry 1993, 456, 45-47, Osaka, Japan.
Humphries et al., "Investigations into the Mechanism of Activation and Initiation of Ethylene Polymerization by Bis (imino)pyridine Cobalt Catalysts: Synthesis, Structures, and Deuterium Labeling Studies," Organometallics 2005, 24, 2039-2050, London, United Kingdom.
Fernandez et al., "Synthesis and Reactions of Dihydrido(triethylalllyl)(1,5-cyclooctadiene)-Iridium(III) Complexes: Catalysts for Dehydrogneative Silylation of Alkenese," Organometallics, 1986, 5, 1519-1520.
Chen et al., "General Synthesis of Di-u-oxo Dimanganese Complexes as Functional Models for the Oxygen Evolving Complex of Photosystem II" Inorg. Chem. 2005, 44, 7661-7670.
Bowman et al., "Synthesis and Molecular and Electronic Structures of Reduced Bis(imino) pyridine Cobalt Dinitrogen Complexes: Ligand versus Metal Reduction," J. Am. Chem. Soc., 2010, 132, 1676-1684, Germany.
ISA / EPO, International Search Report and Written Opinion prepared for PCT/US2014/066338 dated Mar. 2, 2015.
Atienza, et al., "Olefin hydrosilylation and dehydrogenative silylation with bis(imino) pyridine iron and cobalt catalysts," Abstracts of Papers, 244th ACS National Meeting & Exposition, Philadelphia, PA, Aug. 19-23, 2013.
Atienza, "Reactivity of Bis(Iminio)Pyridine Cobalt Complexes in C—H Bond Activation and Catalytic C—C and C—Si Bond Formation" PhD thesis, Jun. 2013, Princeton University.
Shaikh et al., "Iron-Catalyzed Enantioselevtive Hydrosilylation of Keytones," Angew. Chem. Int. Ed., 2008, 47, 2497-2501.
De Bo et al., "Hydrosilylation of Alkynes Mediated by N—heterocyclic Carben Platinum(0) Complexes," Organometallics 2006, 25, 1881-1890.
Boudjouk et al., "Exclusive $\beta$-hydrosilylation of acrylates catalysed by copper-tetramethylethylenediamine," Journal of Organometallic Chemistry, Jan. 1, 1993, pp. 41-43.
Brookhart et al., "Mechanism of a cobalt(III)-catalyzed olefin hydrosilation reaction: direct evidence for a silyl migration pathway," J. Am. Chem. Soc. 1993, 115, 2151.
Castro, Pascel M. et al., "Iron-Based Catalysts Bearing Bis(imido)-Pyridine Ligands for the Polymerization of tert-Butyl Acrylate," Journal of Polymer Science: Part A: Polymer Chemistry, vol. 41, pp. 1380-1389 (2003).
Cornish, et al., "Homogeneous catalysis: VI. Hydrosilylation using tri(pentanedionato)rhodium(III) or tetrakis($\mu$-acetato) Dirhodium(II) as Catalysis," Journal of Organometallic Chemistry, Elsevier-Sequoia S.A. Lausanne, CH, vol. 172, No. 2, Jun. 12, 1979, pp. 153-163.
Chuit et al., "Reactivity of penta- and hexacoordinate silicon compounds and their role as reaction intermediates." Chem. Rev. 1993, 93, 1371-1448.
De Rycke et al., "Toward reactant encapsulation for substrate-selectivity," Tetrahedron Lett. 2012, 53, 462.
Doucette, "Homogeneous Iron Catalysts With Redox-Active Ligands: Synthesis and Electronic Structure," Dissertation Cornell University, Aug. 2006.

(56) References Cited

OTHER PUBLICATIONS

Doyle et al., "Addition/Elimination in the Rhodium(II) Perfluorobutyrate Catalyzed Hydrosilylationo of 1-Alkenes. Rhodium Hydride Promoted Isomerization and Hydrogenation," Organometallics, 1992, 11, 549-555, San Antonio, Texas.

Falck, J. R. et al. "Iridium-Catalyzed (Z)-Trialkylsilylation of Terminal Olefins," J. Org. Chem. 2010, 75, 1701.

Figgins et al., "Complexes of Iron(II), Cobalt(II) and Nickel(II) with Biacetyl-bis-methlylimine, 20Pyridinal-methylimine and 2,6-Pyridindial-bis-methylimine" J. Am. Chem. Soc. 1960, vol. 82, 820-824.

Gandon, et al., "Silicon-Hydrogen Bond Activation and Hydrosilylation of Alkenes Mediated by CpCo Complexes: A Theoretical Study," J. Am. Chem. Soc. 2009, 131, 3007.

Hori et al, "Ruthenium Complex-Catalyzed Silylation of Olefins. Selective Sysnthesis of Allysilanes," Bull. Chem. Soc. Jpn., 1988, 61, 3011-3013, Kyoto, Japan.

Itoh et al, "Disproportionation reactions of organohydrosilanes in the presence of base catalysts" J. Organomet. Chem., 2001, 629, 1-6.

Ivchenko et al., "A convenient approach for the synthesis of 2,6-diformyl- and 2,6-diacetylpyridines," Tetrahedron Lett. 2013, 54, 217.

Fruchtel et al; "Organic Chemistry on Solid Supports," Angewandte Chemie International Edition in English, 1996, vol. 35, Issue 1, pates 17-42.

Junge et al., "Iron-Catalyzed Reducation of Carboxylic Esters to Alcohols," European Journal of Organic Chemistry, vol. 2013, No. 11, Mar. 1, 2013, pp. 2016-2065.

Knijnenburg et al., "Olefin hydrogenation using diimine pyridine complexes of Co and Rh," Journal of Molecular Catalysis, 232 (2005), No. 1-2, pp. 151-159.

Marciniec, Bogdan, "Catalysis by Transition Metal Complexes of Alkene Silylation—Recent Progress and Mechanistic Implications," Coordination Chemistry Reviews, 249 (2009) 2374-2390.

Marciniec et al. "Encyclopedia of Catalysis" pp. 6,7, and 20, Mar. 5, 2010.

Martinez, Remi et al., "C—C Bond Formation via C—H Bond Activation Using an in Situ-Generated Ruthenium Catalyst," Journal of the American Chemical Society, vol. 131, pp. 7887-7895 (2009).

McAtee et al, "Rational Design of a Second Generation Catalyst for Preparation of Allylsilanes Using the Silyl-Heck Reaction," J. Am. Chem. Soc. 2014, 136 (28), 10166-10172.

Bareille et al., "First Titanium-Catalyzed anti-1,4-Hydrosilylation of Dienes," Organometallics, 2005, 24(24), 5802-5806.

Nishiyama et al., "An Iron-Catalysed Hydrosilylation of Ketones," Chem. Commun., Royal Society of Chemistry, 2007, 760-762.

Furuta et al., "Highly efficient catalytic system for hydrosilylation of ketones with iron(II) acetale-thiophenecarboxylate," Tetrahedron Letters, 2008, vol. 49, Issue 1, pp. 110-113.

Ojima et al., "Regioselective hydrosilylation of 1,3-dienes catalyzed by phosphine complexes of palladium and rhodium," J. Organomet. Chem. 1978, 157, 359-372.

Pettigrew, "Synthetic Lubricants and High Performance Fluids, Ch. 12 Silahydrcarbons" (second edition), L. R. Rudnick and L. R. Shubkin (Editors), Marcel Dekker, NY 1999, pp. 287-296.

Poyatos, Macarena et al., "Coordination Chemistry of a Modular N,C-Chelating Oxazole-Carbene Ligand and Its Applications in Hydrosilylation Catalysis," Organometallics, vol. 25, pp. 2634-2641 (2006).

Reiff, W. M. et al., "Mono(2,2',2"-terpyridine) Complexes of Iron(II)," Journal of Inorganic Chemistry, vol. 8, No. 9, pp. 2019-2021 (1969).

Parker et al. "1,2-Selective Hydrosilylation of Conjugated Dienes," J. Am. Chem. Soc., 2014, 136 (13), pp. 4857-4860.

Benkeser et al., "Chloroplatinic acid catalyzed additions of silanes to isoprene," J. Organomet. Chem. 1978, 156, 235-244.

Schmidt, Roland et al., "Heterogenized Iron(II) Complexes as Highly Active Ethene Polymerization Catalysts," Journal of Molecular Catalysis A: Chemical, vol. 179, pp. 155-173 (2002).

Shaikh et al., "A Convenient and General Iron-Catalyzed Hydrosilylation of Aldehydes," Organic Letters, vol. 9, No. 26, Dec. 1, 2007, pp. 5429-5432.

Small, B. L., et al. "Highly Active Iron and Cobalt Catalysts for the Polymerization of Ethylene," J. Am. Chem. Soc. 1998, 120(16), 4049-4050.

Greenhalgh et al.,"Iron-Catalysed Chemo-, Regio-, and Stereoselective Hydrosilylation of Alkenes and Alkynes using a Bench-Stable Iron(II) Pre-Catalyst," Adv. Synth. Cata. 2014, 356(2-3), 584-590.

Woo et al., "Redistribution of Bos- and Tris(silyl)methanes Catalyzed by Red-Al," Bull. Korean. Chem. Soc. 1996, 17, 123-125.

Wu et al., "A Strategy for the Synthesis of Well-Defined Iron Catalysts and Application to Regioselective Diene Hydrosilylation," Journal of the American Chemical Society, vol. 132, No. 38. Sep. 29, 2010, pp. 13214-13216.

Yi, Chae S. et al., "Regioselective Intermolecular Coupling Reaction of Arylketones and Alkenes Involving C—H Bond Activation Catalyzed by an in Situ Formed Cationic Ruthenium Hydride Complex," Organometallics, vol. 28, pp. 4266-4268 (2009).

Zhang et al., "Ferrous and Cobaltous Chlorides Bearing 2,8-Bis(imino)quinolines: Highly Active Catalysts for Ethylene Polymerization at High Temperature," Organometallics, vol. 29, pp. 1168-1173 (2010).

Zhu et al., "(Py)2Co(CH2SiMe3)2 As an Easily Accessible Source of "CoR2"," Organometallics, 2010, 29 (8), 1897-1908.

\* cited by examiner

COBALT CATALYSTS AND THEIR USE FOR HYDROSILYLATION AND DEHYDROGENATIVE SILYLATION

CROSS REFERENCE TO RELATED APPLICATIONS

This application claims priority to U.S. Provisional Application No. 61/906,204, filed on Nov. 19, 2013 entitled "Cobalt Catalysts and Their Use for Hydrosilylation and Dehydrogenative Silylation" and U.S. Provisional Application No. 62/031,463 filed on Jul. 31, 2014 entitled "Terpyridine Cobalt Complexes and Their Use as Catalysts," the entire disclosures of which are incorporated herein by reference in their entireties.

FIELD OF THE INVENTION

This invention relates generally to transition metal-containing compounds, more specifically to cobalt complexes containing terpyridine ligands and their use as catalysts for hydrosilylation and dehydrogenative silylation reactions.

BACKGROUND OF THE INVENTION

Hydrosilylation chemistry, typically involving a reaction between a silyl hydride and an unsaturated organic group, is the basis for synthetic routes to produce commercial silicone-based products like silicone surfactants, silicone fluids and silanes as well as many addition cured products like sealants, adhesives, and coatings. Typical hydrosilylation reactions use precious metal catalysts to catalyze the addition of a silyl-hydride (Si—H) to an unsaturated group, such as an olefin. In these reactions, the resulting product is a silyl-substituted, saturated compound. In most of these cases, the addition of the silyl group proceeds in an anti-Markovnikov manner, i.e., to the less substituted carbon atom of the unsaturated group. Most precious metal catalyzed hydrosilylations only work well with terminally unsaturated olefins, as internal unsaturations are generally non-reactive or only poorly reactive. There are currently only limited commercially viable methods for the general silylation of olefins where after the addition of the Si—H group there still remains an unsaturation in the original substrate. This reaction, termed a dehydrogenative silylation, has potential uses in the synthesis of new silicone materials, such as silanes, silicone fluids, crosslinked silicone elastomers, and silylated or silicone-crosslinked organic polymers such as polyolefins, unsaturated polyesters, and the like.

Various precious metal complex catalysts are known in the art including a platinum complex containing unsaturated siloxanes as ligands, which is known in the art as Karstedt's catalyst. Other platinum-based hydrosilylation catalysts include Ashby's catalyst, Lamoreaux's catalyst, and Speier's catalyst.

Other metal-based catalysts have been explored including, for example, rhodium complexes, iridium complexes, palladium complexes and even first-row transition metal-based catalysts to promote limited hydrosilylations and dehydrogenative silylations.

U.S. Pat. No. 5,955,555 discloses the synthesis of certain iron or cobalt pyridine di-imine (PDI) complexes bearing two anionic ligands. The preferred anions are chloride, bromide, and tetrafluoroborate. U.S. Pat. No. 7,442,819 discloses iron and cobalt complexes of certain tricyclic ligands containing a "pyridine" ring substituted with two imino groups. U.S. Pat. Nos. 6,461,994, 6,657,026 and 7,148,304 disclose several catalyst systems containing certain transitional metal-PDI complexes. U.S. Pat. No. 7,053,020 discloses a catalyst system containing, inter alia, one or more bisarylimino pyridine iron or cobalt catalyst. Chirik et al describe bisarylimino pyridine cobalt complexes with anionic ligands (Inorg. Chem. 2010, 49, 6110 and JACS. 2010, 132, 1676.) However, the catalysts and catalyst systems disclosed in these references are described for use in the context of olefin hydrogenation, polymerizations and/or oligomerisations, not in the context of dehydrogenative silylation reactions. U.S. Pat. No. 8,236,915 discloses hydrosilylation using Mn, Fe, Co, and Ni catalysts containing pyridinediimine ligands. However, these catalysts are sensitive to air and must be handled in a glove box.

There is a continuing need in the silylation industry for non-precious metal-based catalysts that are effective for efficiently and selectively catalyzing hydrosilylation and/or dehydrogenative silylations. There is also a need for metal-based catalysts that are air stable. Many metal-based catalysts, including those based on iron or cobalt, are not stable under atmospheric conditions. This makes such materials generally unsuitable for application on a production or industrial scale.

Further, many industrially important homogeneous metal catalysts suffer from the drawback that following consumption of the first charge of substrates, the catalytically active metal is lost to aggregation and agglomeration and its beneficial catalytic properties are substantially diminished via colloid formation or precipitation. This is a costly loss, especially for noble metals such as Pt. Heterogeneous catalysts are used to alleviate this problem but have limited use for polymers and also have lower activity than homogeneous counterparts. For example, the two primary homogeneous catalysts for hydrosilylation, Speier's and Karstedt's, often lose activity after catalyzing a charge of olefin and silyl- or siloxy-hydride reaction. If a single charge of the homogeneous catalyst could be re-used for multiple charges of substrates, then catalyst and process cost advantages would be significant.

SUMMARY OF THE INVENTION

In one aspect, the present invention provides a complex of the Formula:

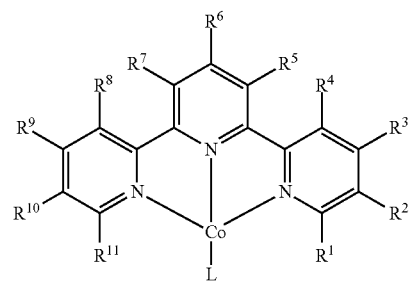

wherein each occurrence of $R^1$-$R^{11}$ is independently hydrogen, a C1-C18 alkyl, a C1-C18 substituted alkyl, a C5-C18 cycloalkyl, a C5-C18 substituted cycloalkyl, a C6-C18 aryl, a substituted C6-C18 aryl, or an inert substituent wherein one or more of $R^1$-$R^{11}$, other than hydrogen, optionally contain at least one heteroatom; optionally any two of $R^1$-$R^{11}$ vicinal to one another, $R^4$-$R^5$, and/or $R^7$-$R^8$ taken together may form a ring being a substituted or unsubstituted, saturated, or unsaturated cyclic structure; and L is chosen from hydrogen, a C1-C18 alkyl, C1-C18 substituted alkyl, a C6-C18 aryl, a substituted C6-C18 aryl group, an alkaryl group, an aralkyl group, or an alkyl trialkylsilyl, where L optionally contains at least one heteroatom.

In one embodiment, $R^1$-$R^{11}$ are hydrogen.

In one embodiment, L is —C($R^{22}$)$_2$—Si($R^{23}$)$_3$ where $R^{22}$ and $R^{23}$ are independently hydrogen, a C1-C18 alkyl, a C1-C18 substituted alkyl, a C6-C18 aryl, a substituted C6-C18 aryl, or an inert substituent, and $R^{22}$ and $R^{23}$ optionally contain at least one heteroatom.

In one embodiment, wherein $R^1$-$R^{11}$ are hydrogen.

In one embodiment, the catalyst is of the formula:

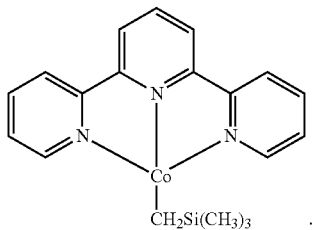

In one embodiment, at least one of $R^1$-$R^{11}$ is chosen from an aryl group or a substituted aryl group. In one embodiment, the substituted aryl group is chosen from tolyl, xylyl, naphthyl, mesityl, aniline, fluorophenyl, or a combination of two or more thereof.

In one embodiment, $R^1$-$R^5$ and $R^7$-$R^{11}$ are hydrogen, and $R^6$ is chosen from pyrrolidino, flourophenyl, aniline, or mesityl.

In one embodiment, the complex is of the formula:

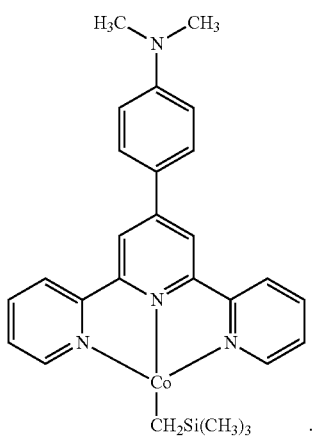

In one aspect, the present invention provides a process for producing a silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the silylated product, wherein the catalyst is a complex of the Formula (IV) or an adduct thereof:

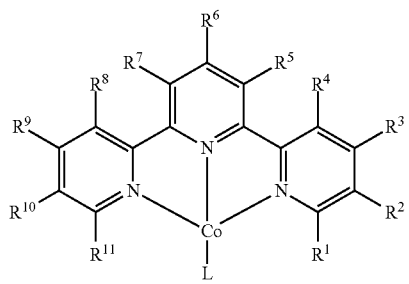

wherein each occurrence of $R^1$-$R^{18}$ is independently hydrogen, a C1-C18 alkyl, a C1-C18 substituted alkyl, a C5-C18 cycloalkyl, a C5-C18 substituted cycloalkyl, a C6-C18 aryl, a substituted C6-C18 aryl, or an inert substituent wherein one or more of $R^1$-$R^{11}$, other than hydrogen, optionally contain at least one heteroatom; optionally any two of $R^1$-$R^{11}$ vicinal to one another, $R^4$-$R^5$, and/or $R^7$-$R^8$ taken together may form a ring being a substituted or unsubstituted, saturated, or unsaturated cyclic structure; and L is chosen from hydrogen, a C1-C18 alkyl, C1-C18 substituted alkyl, a C6-C18 aryl, a substituted C6-C18 aryl group, an alkaryl group, or an aralkyl group, an alkyl trialkylsilyl, where L optionally contains at least one heteroatom.

In one embodiment, $R^1$-$R^{11}$ are hydrogen.

In one embodiment, L is —C($R^{22}$)$_2$—Si($R^{23}$)$_3$ where $R^{22}$ and $R^{23}$ are independently hydrogen, a C1-C18 alkyl, a C1-C18 substituted alkyl, a C6-C18 aryl, a substituted C6-C18 aryl, or an inert substituent, and $R^{22}$ and $R^{23}$ optionally contain at least one heteroatom.

In one embodiment, $R^1$-$R^{11}$ are hydrogen.

In one embodiment, the catalyst is of the formula:

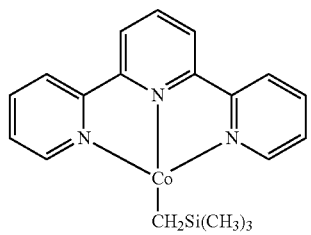

In one embodiment, at least one of $R^1$-$R^{11}$ is chosen from an aryl group or a substituted aryl group.

In one embodiment, the substituted aryl group is aniline.

In one embodiment, the complex is of the formula:

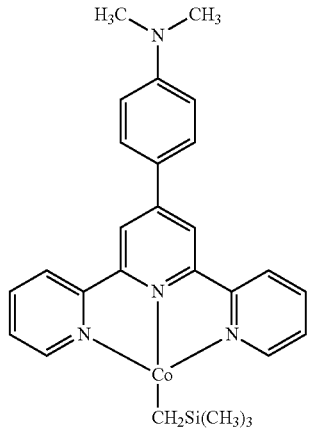

In one embodiment, the process comprises removing the complex and/or derivatives thereof from the silylated product.

In one embodiment, the silylated product comprises a hydrosilylation product.

In one embodiment, the silylated product comprises a dehydrogenatively silylated product.

In one embodiment, the silylated product comprises a mixture of (i) a hydrosilylation product, and (ii) a dehydrogenative silylated product.

In one embodiment, the unsaturated compound (a) is chosen from a linear or branched olefin; a cycloalkene; an alkyl-capped allyl polyether; a vinyl-functional alkyl-capped allyl or methallyl polyether; an alkyl-capped terminally unsaturated amine; an alkyne; a terminally unsaturated acrylate or methacrylate; an unsaturated aryl ether; a vinyl-functionalized polymer or oligomer; a vinyl-functionalized and/or terminally-unsaturated alkenyl-functional silane; and/or silicone; an unsaturated fatty acid; an unsaturated ester; or combinations of two or more thereof.

In one embodiment, the reaction is conducted under an inert atmosphere.

In one embodiment, the reaction is carried out at a temperature of −10° C. to 300° C.

In one embodiment, the silyl hydride comprises a hydride fluid chosen from one or a combination of compounds of the formulas:

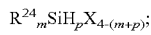

$R^{24}{}_m SiH_p X_{4-(m+p)}$;

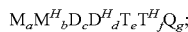

$M_a M^H{}_b D_c D^H{}_d T_e T^H{}_f Q_g$;

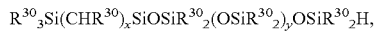

$R^{30}{}_3 Si(CHR^{30})_x SiOSiR^{30}{}_2 (OSiR^{30}{}_2)_y OSiR^{30}{}_2 H$,

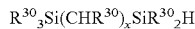

$R^{30}{}_3 Si(CHR^{30})_x SiR^{30}{}_2 H$ where each $R^{24}$ is independently a substituted or unsubstituted aliphatic or aromatic hydrocarbyl group; X is halogen, alkoxy, acyloxy, or silazane; m is 0-3; p is 1-3, with the proviso that the tetrvalency of silicon is preserved; M represents a monofunctional group of formula $R^{25}{}_3 SiO_{1/2}$; a D represents a difunctional group of formula $R^{25}{}_2 SiO_{2/2}$; a T represents a trifunctional group of formula $R^{25} SiO_{3/2}$; Q represents a tetrafunctional group of formula $SiO_{4/2}$; $M^H$ represents $HR^{25}{}_2 SiO_{1/2}$, $T^H$ represents $HSiO_{3/2}$, and $D^H$ group represents $R^{25} HSiO_{2/2}$; each occurrence of $R^{25}$ is independently a $C_1$-$C_{18}$ alkyl, a $C_1$-$C_{18}$ substituted alkyl, a $C_6$-$C_{14}$ aryl or substituted aryl, wherein $R^{25}$ optionally contains at least one heteroatom; subscripts a, b, c, d, e, f, and g are such that the molar mass of the compound is between 100 and 100,000 Dalton; each occurrence of $R^{30}$ is independently a C1-C18 alkyl, a C1-C18 substituted alkyl, a C6-C14 aryl or substituted aryl; x is 1-8, and y is 0-10.

In one embodiment, the complex is immobilized on a support. In one embodiment, the support is chosen from carbon, silica, alumina, $MgCl_2$, zirconia, polyethylene, polypropylene, polystyrene, poly(aminostyrene), sulfonated polystyrene, or a combination of two or more thereof.

In one aspect, the present invention provides a composition produced by the process of claim 10, wherein the composition contains the catalyst or derivatives thereof. In one embodiment, the composition comprises at least one component selected from the group of silanes, silicone fluids, and crosslinked silicones, or a combination of two or more thereof.

In one aspect, the invention provides a complex of Formula (IV)

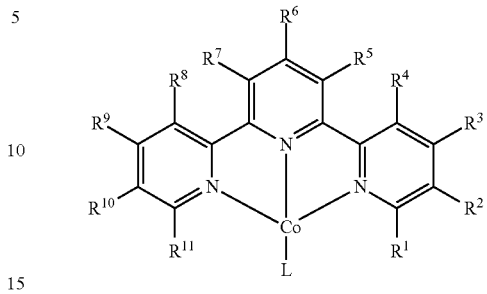

wherein each occurrence of $R^1$-$R^{11}$ is independently hydrogen, a C1-C18 alkyl, a C1-C18 substituted alkyl, a C6-C18 aryl, a substituted C6-C18 aryl, or an inert substituent wherein one or more of $R^1$-$R^{11}$, other than hydrogen, optionally contain at least one heteroatom; optionally any two of $R^1$-$R^{11}$ vicinal to one another, $R^4$-$R^5$, and/or $R^7$-$R^8$ taken together may form a ring being a substituted or unsubstituted, saturated, or unsaturated cyclic structure; and L is chosen from hydrogen, a C1-C18 alkyl, C1-C18 substituted alkyl, a C6-C18 aryl, a substituted C6-C18 aryl group, an alkaryl group, an aralkyl group, an alkyl trialkylsilyl, where L optionally contains at least one heteroatom.

In another aspect, the invention provides a process of silylating a composition comprising contacting silylation reactants with a complex of Formula (IV). In one embodiment, the product of the silylation reaction is a hydrosilylated product, a dehydrogenative silylated product, or a combination thereof.

DETAILED DESCRIPTION OF THE INVENTION

The invention relates to cobalt complexes containing terpyridine ligands and their use as efficient hydrosilylation catalysts and/or dehydrogenative silylation and catalysts. In one embodiment of the invention, there is provided a complex of the Formula (I), as illustrated above, wherein Co can be in any valence or oxidation state (e.g., +1, +2, or +3) for use in a hydrosilylation and/or dehydrogenative silylation and crosslinking reactions. In one embodiment, a complex of Formula (IV) is provided for use in a hydrosilylation and/or dehydrogenative silylation. In particular, according to one embodiment of the invention, a class of cobalt terpyridine complexes has been found that are capable of hydrosilylation and/or dehydrogenative silylation reactions. The invention also addresses the advantage of reusing a single charge of catalyst for multiple batches of product, resulting in process efficiencies and lower costs.

As used herein, the term "alkyl" includes straight, branched and cyclic alkyl groups. Specific and non-limiting examples of alkyls include, but are not limited to, methyl, ethyl, propyl, isobutyl, and cyclohexyl.

As used herein, the term "substituted alkyl" includes an alkyl group that contains one or more substituent groups that are inert under the process conditions to which the compound containing these groups is subjected. The substituent groups also do not substantially or deleteriously interfere with the process.

As used herein, the term "aryl" refers to a non-limiting group of any aromatic hydrocarbon from which one hydrogen atom has been removed. An aryl may have one or more aromatic rings, which may be fused, connected by single bonds or other groups. Examples of suitable aryls include, but are not limited to, tolyl, xylyl, phenyl and naphthalenyl.

As used herein, the term "substituted aryl" refers to an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the attachment can be through a heteroatom (such as nitrogen) of the heteroaromatic ring instead of a carbon. In one embodiment, the substituted aryl groups herein contain 1 to about 30 carbon atoms.

As used herein, the term "alkenyl" refers to any straight, branched, or cyclic alkenyl group containing one or more carbon-carbon double bonds, where the point of substitution can be either a carbon-carbon double bond or elsewhere in the group. Examples of suitable alkenyls include, but are not limited to, vinyl, propenyl, allyl, methallyl, ethylidenyl norbornyl, etc.

As used herein, the term "alkynyl" refers to any straight, branched, or cyclic alkynyl group containing one or more carbon-carbon triple bonds, where the point of substitution can be either at a carbon-carbon triple bond or elsewhere in the group.

As used herein, the term "unsaturated" refers to one or more double or triple bonds. In one embodiment, it refers to carbon-carbon double or triple bonds.

As used herein, the term "inert substituent" refers to a group other than hydrocarbyl or substituted hydrocarbyl, which is inert under the process conditions to which the compound containing the group is subjected. The inert substituents also do not substantially or deleteriously interfere with any process described herein that the compound in which they are present may take part in. Examples of inert substituents include, but are not limited to, halo (fluoro, chloro, bromo, and iodo), and ether such as —$OR^{30}$ wherein $R^{30}$ is hydrocarbyl or substituted hydrocarbyl.

As used herein, the term "hetero atoms" refers to any of the Group 13-17 elements except carbon, and can include, for example, oxygen, nitrogen, silicon, sulfur, phosphorus, fluorine, chlorine, bromine, and iodine.

As used herein, the term "olefin" refers to any aliphatic or aromatic hydrocarbon also containing one or more aliphatic carbon-carbon unsaturations. Such olefins may be linear, branched, or cyclic and may be substituted with heteroatoms as described above, with the proviso that the substituents do not interfere substantially or deleteriously with the course of the desired reaction to produce the dehydrogenatively silylated or hydrosilylated product.

Cobalt Complexes

The present invention provides, in one aspect, a cobalt complex, which complex can be used as a catalyst in hydrosilylation or dehydrogenative silylation reactions. In one embodiment, the catalyst composition comprises a cobalt complex containing a terpyridine ligand and a chelating alkene-substituted silyl ligand coordinated to the cobalt, with the alkenyl substitution preferred at the beta-position relative to silicon. In one embodiment, the catalyst is a complex of the Formula (I) or an adduct thereof:

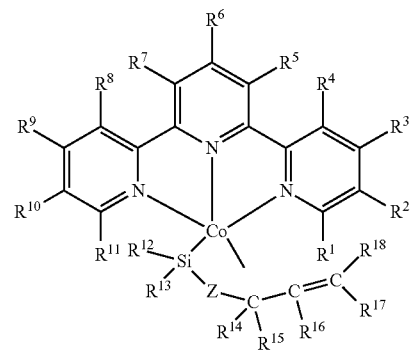

(I)

wherein each occurrence of $R^1$-$R^{18}$ is independently hydrogen, a C1-C18 alkyl, a C1-C18 substituted alkyl, a C6-C18 aryl, a substituted C6-C18 aryl, or an inert substituent; optionally any two of $R^1$-$R^{11}$ vicinal to one another, $R^4$-$R^5$, and/or $R^7$-$R^8$ taken together may form a ring being a substituted or unsubstituted, saturated, or unsaturated cyclic structure; and Z is O, $NR^{19}$, or $CR^{20}R^{21}$, wherein $R^{19}$, $R^{20}$, and $R^{21}$ is independently hydrogen, a C1-C18 alkyl, C1-C18 substituted alkyl, a C6-C18 aryl, a substituted C6-C18 aryl group, an alkaryl group, an aralkyl group, $R^{19}$, $R^{20}$, and $R^{21}$ optionally contains at least one heteroatom. In the catalyst complex Co can be in any valence or oxidation state (e.g., +1, +2, or +3).

In one embodiment, $R^{12}$ and $R^{13}$ are independently chosen from a C1-C10 alkyl, or a C6-C18 aryl; Z is O; and $R^{14}$-$R^{18}$ are hydrogen. In one embodiment, $R^{12}$ and $R^{13}$ are each methyl. In still another embodiment, $R^{12}$ and $R^{13}$ are each phenyl.

In one embodiment, the cobalt complex is a complex of the formula:

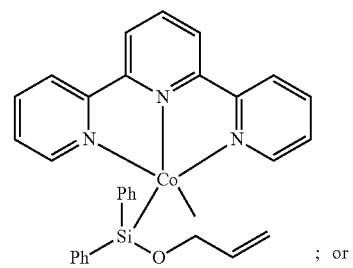

(II)

; or

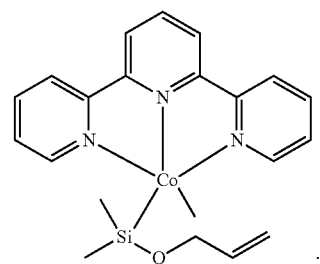

(III)

In one embodiment, the catalyst is generated by reacting a catalyst precursor prepared according to published procedure with the desired alkenyl-modified silane containing a SiH group in a solvent. Catalysts can be prepared by any suitable method now known to a person skilled in the field or later discovered. For example, the catalysts can be prepared by reacting a terpyridine ligand with a metal complex such as $Py_2Co(CH_2TMS)_2$ in a solvent (such as pentane) with stirring at room temperature. The resulting complex may be treated with an ether to yield a mono complex, which can then be treated with the desired alkenyl-modified silane in a solvent (e.g., toluene).

The cobalt catalysts with the terpyridine and alkene-modified silyl ligands exhibit good stability to air at atmospheric conditions. The present catalysts exhibit air stability that allows handling in the open atmosphere. Many iron or cobalt complexes known-previously to catalyze hydrosilylation or dehydrogenative silylation exhibit poor air stability rendering them impractical for industrial use. The present Terpy-Co complexes with the chelating alkene-modified silyl ligand, however, have been found to overcome this major drawback.

In another aspect, a terpyridine based cobalt complex with a single or mono ligand, L, coordinated to the cobalt is provided and which may also be used in a silylation process. The terpyridine cobalt mono-ligand complexes may have the empirical formula $(C_{15}R_{11}N_3)Co(L)$, where each occurrence of "R" and L is independently chosen from hydrogen, a C1-C18 alkyl, a C1-C18 substituted alkyl, a C6-C18 aryl, a substituted C6-C18 aryl, or an inert substituent, and "R," other than hydrogen, optionally contain at least one heteroatom.

In one embodiment, the mono-ligand complex is a compound of the formula:

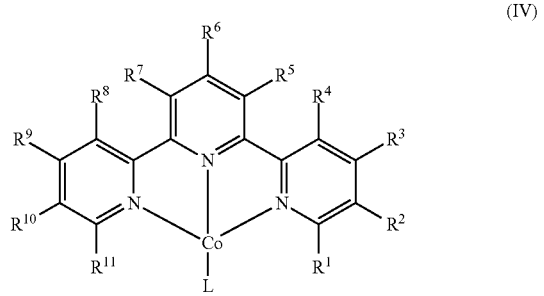

where $R^1$-$R^{11}$ are independently hydrogen, a C1-C18 alkyl, a C1-C18 substituted alkyl, a C5-C18 cycloalkyl, a C5-C18 substituted cycloalkyl, a C6-C18 aryl, a substituted C6-C18 aryl, or an inert substituent, $R^1$-$R^{11}$ optionally containing one or more heteroatoms; optionally any two of $R^1$-$R^{11}$ vicinal to one another, $R^4$-$R^5$, and/or $R^7$-$R^8$ taken together may form a ring being a substituted or unsubstituted, saturated, or unsaturated cyclic structure; and L is chosen from hydrogen, a C1-C18 alkyl, C1-C18 substituted alkyl, a C6-C18 aryl, a substituted C6-C18 aryl group, an alkaryl group, an aralkyl group, an alkyl trialkylsilyl, where L optionally contains at least one heteroatom. In one embodiment, one or more of $R^1$-$R^{11}$ may be a phenyl, alkyl substituted phenyl, hydroxyphenyl, anilines, naphthalene, etc. Non-limiting examples of a suitable substituted phenyl include phenyl groups comprising one or more C1-C10 alkyl substituents including, limited to, methyl, ethyl, propyl, isopropyl, butyl, etc. Examples of suitable alkyl phenyl groups include, but are not limited to tolyl, xylyl, naphthyl, etc. Still other examples of suitable substituted aryl groups include halo substituted aryl such as, for example, fluoro substituted aryl compounds. In another embodiment, $R^1$-$R^{11}$ may be chosen from a heterocyclic compound. Examples of suitable heterocyclic compounds include, but are not limited to, nitrogen-containing rings. A non-limiting example of suitable heterocyclic group is the pyrrolidino group.

In one embodiment, L is chosen from an alkyl trialkylsilyl group. In one embodiment, the alkyl trialkylsilyl group has the formula $-C(R^{22})_2-Si(R^{23})_3$, and the complex is of the formula:

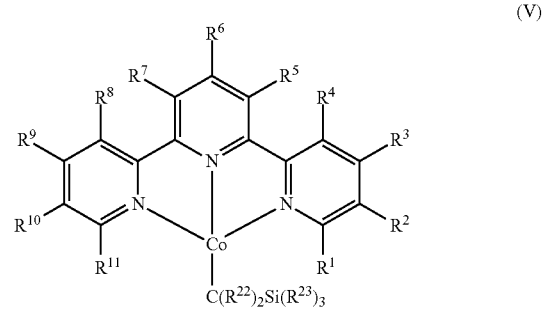

where each occurrence of $R^{22}$ and $R^{23}$ are independently hydrogen, a C1-C18 alkyl, a C1-C18 substituted alkyl, a C6-C18 aryl, a substituted C6-C18 aryl, or an inert substituent, and $R^{22}$ and $R^{23}$ optionally contain at least one heteroatom. Examples of suitable alkyl groups include, but are not limited to, methyl, ethyl, propyl, isopropyl, butyl, pentyl, etc. Examples of suitable aryl groups include, but are not limited to, phenyl, alkyl substituted phenyl, hydroxyphenyl, anilines, naphthalene, etc. In one embodiment, $R^1$-$R^{11}$ are each hydrogen. In one embodiment, at least one of $R^1$-$R^{11}$ comprises an aryl group. In one embodiment, at least one of $R^1$-$R^{11}$ comprises an aniline group. In one embodiment, $R^6$ is advantageously fluorophenyl, dimethylaminophenyl, mesityl, or the pyrrolidino group. The $-C(R^{22})_2-Si(R^{23})_3$ group may also be referred to as a neosilyl group and may be abbreviated "Ns".

Non-limiting examples of suitable compounds of Formula (IV) include:

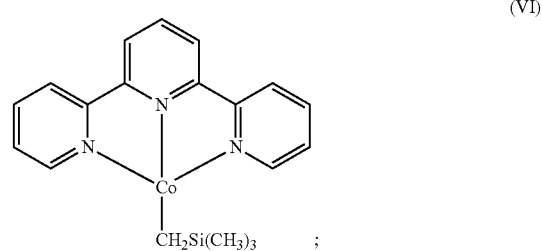

and

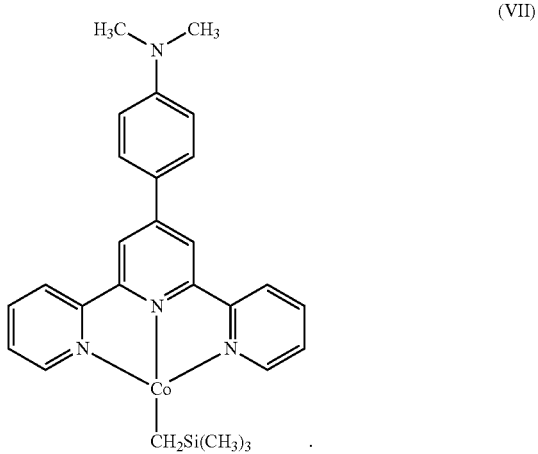

(VII)

Various methods can be used to prepare the catalyst utilized in the process of the present invention. The complexes of Formula (IV) may be made reacting a terpyridine ligand with a metal complex such as $Py_2Co(CH_2TMS)_2$ in a solvent (such as pentane) with stirring at room temperature. Py is an abbreviation for pyridine and TMS refers to the trimethylsilyl group. The resulting complex may be treated with an ether to yield a mono complex. In one embodiment, complexes of Formula (IV) may be made by dissolving a terpyridine or terpyridine-based ligand in a solvent compatible with a $(Py)_2Co(CR'_2SiR''_3)_2$ solution, where R' and R" are independently hydrogen, a C1-C18 alkyl, a C1-C18 substituted alkyl, a C6-C18 aryl, a substituted C6-C18 aryl, or an inert substituent, and $R^{22}$ and $R^{23}$ optionally contain at least one heteroatom; combining the terpyridine solution and a $(Py)_2Co(CR'_2SiR''_3)_2$ solution cooled to between approximately 0° C. and −100° C. and stirring and fully evacuating, dissolving the residual and filtering; combining the filtered product with a solvent and stirring; and recrystallizing from a water insoluble liquid or mixture, at temperatures between approximately 0° C. and −100° C. In one embodiment, the catalyst is generated in-situ by contacting a catalyst precursor with an activator in the presence of a liquid medium containing at least one component selected from the group consisting of a solvent, the silyl hydride, the compound containing at least one unsaturated group, and combinations thereof.

In the silylation reaction processes, the catalysts can be unsupported or immobilized on a support material, for example, carbon, silica, alumina, $MgCl_2$ or zirconia, or on a polymer or prepolymer, for example polyethylene, polypropylene, polystyrene, poly(aminostyrene), or sulfonated polystyrene. The metal complexes can also be supported on dendrimers. In some embodiments, for the purposes of attaching the metal complexes of the invention to a support, it is desirable that at least one of $R^1$ to $R^{11}$ of the metal complexes, has a functional group that is effective to covalently bond to the support. Exemplary functional groups include but are not limited to vinyl, SH, COOH, $NH_2$ or OH group.

Catalyzed Reactions

In accordance with the present invention, the cobalt catalysts of Formula (I) or Formula (IV) can be used as a catalyst for a hydrosilylation process or a dehydrogenative silylation process. Each process generally comprises reacting (a) a silyl hydride compound with (b) an unsaturated compound having at least one unsaturated functional group.

The silyl hydride employed in the reactions is not particularly limited. It can be, for example, any compound chosen from hydrosilanes or hydrosiloxanes including those compounds of the formulas $R^{24}_m SiH_p X_{4-(m+p)}$ or $M_a M^H_b D_c D^H_d T_e T^H_f Q_g$, where each $R^{24}$ is independently a substituted or unsubstituted aliphatic or aromatic hydrocarbyl group, X is alkoxy, acyloxy, or silazane, m is 0-3, p is 1-3, (with the proviso that silicon remains tetravalent), and M, D, T, and Q have their usual meaning in siloxane nomenclature. The subscripts a, b, c, d, e, f, and g are such that the molar mass of the siloxane-type reactant is between 100 and 100,000 Dalton. In one embodiment, an "M" group represents a monofunctional group of formula $R^{25}_3 SiO_{1/2}$, a "D" group represents a difunctional group of formula $R^{25}_2 SiO_{2/2}$, a "T" group represents a trifunctional group of formula $R^{25} SiO_{3/2}$, and a "Q" group represents a tetrafunctional group of formula $SiO_{4/2}$, an "$M^H$" group represents $HR^{25}_2 SiO_{1/2}$, a "$T^H$" represents $HSiO_{3/2}$, and a "$D^H$" group represents $R^{25} HSiO_{2/2}$. Each occurrence of $R^{25}$ is independently C1-C18 alkyl, C1-C18 substituted alkyl, C6-C14 aryl or substituted aryl, wherein $R^{25}$ optionally contains at least one heteroatom. In one embodiment, $R^{24}$ is chosen from a C1-C10 alkyl. In one embodiment, X is chosen from a C1-C10 alkoxy.

The instant invention also provides hydrosilylation with hydridosiloxanes comprising carbosiloxane linkages (for example, Si—$CH_2$—Si—O—SiH, Si—$CH_2$—$CH_2$—Si—O—SiH or Si-arylene-Si—O—SiH). Carbosiloxanes contain both the —Si-(hydrocarbylene)-Si— and —Si—O—Si— functionalities, where hydrocarbylene represents a substituted or unsubstituted, divalent alkylene, cycloalkylene or arylene group. The synthesis of carbosiloxanes is disclosed in U.S. Pat. No. 7,259,220; U.S. Pat. No. 7,326,761 and U.S. Pat. No. 7,507,775 all of which are incorporated herein in their entirety by reference. An exemplary formula for hydridosiloxanes with carbosiloxane linkages is $R^{30}_3 Si(CHR^{30})_x SiOSiR^{30}_2 (OSiR^{30}_2)_y OSiR^{30}_2 H$, wherein each occurrence of $R^{30}$ is independently a monovalent alkyl, cycloalkyl or aryl group such as C1-C18 alkyl, C1-C18 substituted alkyl, C6-C14 aryl or substituted aryl. Non-limiting examples of suitable groups include, for example, methyl, ethyl, cyclohexyl or phenyl. Additionally, $R^{30}$ independently may also be H. The subscript x has a value of 1-8, y has a value from zero to 10 and is preferably zero to 4. A specific example of a hydridocarbosiloxane is $(CH_3)_3 SiCH_2 CH_2 Si(CH_3)_2 OSi(CH_3)_2 H$.

Hydridocarbosilanes are another class useful for the hydrosilylation and dehydrogenative silylation reactions of the instant invention. Hydridocarbosilanes have SiH bonds as well as linkages such as —Si—$(CH_2)_x$—Si— (wherein x is an integer greater than or equal to 1, and is preferably 1-8) and other Si-hydrocarbylene groups in the molecular formula, but no siloxane linkages. As defined above, hydrocarbylene refers to a substituted or unsubstituted divalent alkylene, cycloalkylene or arylene group. They can be linear, cyclic or branched and contain more than one SiH bond per molecule. The SiH bonds can be terminal or distributed internally along the Si-hydrocarbylene chains in the molecule. An exemplary formula for hydridocarbosilanes is $R^{30}_3 Si(CHR^{30})_x SiR^{30}_2 H$, $R^{30}$ and x having the meanings defined above. Specific examples of hydridocarbosilanes are $(CH_3)_3 SiCH_2 CH_2 Si(CH_3)_2 H$, $H(CH_3)_2 SiCH_2 CH_2 Si(CH_3)_2 H$, $(CH_3)_3 SiC_6 H_4 Si(CH_3)_2 H$, $(CH_3)_3 SiC_6 H_{10} Si(CH_3)_2 H$, wherein —$C_6 H_4$— is the phenylene linkage and —$C_6 H_{10}$— is the cyclohexylene linkage. Use of hydridocarbosilanes in hydrosilylation and dehydrogenative silylation enables the synthesis of saturated and unsaturated silahydrocarbons as illustrated in Example 15.

The unsaturated compound containing an unsaturated functional group employed in the hydrosilylation reaction is generally not limited and can be chosen from an unsaturated compound as desired for a particular purpose or intended application. The unsaturated compound can be a mono-unsaturated compound or it can comprise two or more unsaturated functional groups. In one embodiment, the unsaturated group can comprise an aliphatically unsaturated functional group. The unsaturated compound can be a mono-unsaturated compound or it can comprise two or more unsaturated functional groups. In one embodiment, the unsaturated group can be an aliphatically unsaturated functional group. Examples of suitable compounds containing an unsaturated group include, but are not limited to, unsaturated polyethers such as alkyl-capped allyl polyethers, vinyl functionalized alkyl capped allyl or methylallyl polyethers; terminally unsaturated amines; alkynes; C2-C45 olefins, in one embodiment alpha olefins; unsaturated epoxides such as allyl glycidyl ether and vinyl cyclohexene-oxide; terminally unsaturated acrylates or methyl acrylates; unsaturated aryl ethers; unsaturated aromatic hydrocarbons; unsaturated cycloalkanes such as trivinyl cyclohexane; vinyl-functionalized polymer or oligomer; and vinyl-functionalized and/or terminally-unsaturated alkenyl-silanes and/or silicones; unsaturated fatty acids; unsaturated fatty esters; or combinations of two or more thereof. Illustrative examples of such unsaturated substrates include, but are not limited to, ethylene, propylene, isobutylene, 1-hexene, 1-octene, 1-octadecene, styrene, alpha-methylstyrene, cyclopentene, norbornene, 1,5-hexadiene, norbornadiene, vinylcyclohexene, allyl alcohol, allyl-terminated polyethyleneglycol, allylacrylate, allyl methacrylate, allyl glycidyl ether, allyl-terminated isocyanate- or acrylate prepolymers, polybutadiene, allylamine, methallyl amine, acetylene, phenylacetylene, vinyl-pendent or vinyl-terminal polysiloxanes, vinylcyclosiloxanes, vinylsiloxane resins, vinyl-functional synthetic or natural minerals, etc.

Unsaturated polyethers suitable for the hydrosilylation reaction include polyoxyalkylenes having the general formula:

$R^{26}(OCH_2CH_2)_z(OCH_2CHR^{28})_w$—$OR^{27}$; and/or

$R^{27}O(CHR^{28}CH_2O)_w(CH^2CH^2O)_z$—$CR^{29}2$-C≡C—

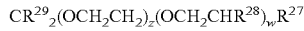
$CR^{29}{}_2(OCH_2CH_2)_z(OCH_2CHR^{28})_wR^{27}$ wherein $R^{26}$ denotes an unsaturated organic group containing from 2 to 10 carbon atoms such as allyl, methylallyl, propargyl or 3-pentynyl. When the unsaturation is olefinic, it is desirably terminal to facilitate smooth hydrosilylation. However, when the unsaturation is a triple bond, it may be internal. $R^{27}$ is independently hydrogen, vinyl, allyl, methallyl, or a polyether capping group of from 1 to 8 carbon atoms such as the alkyl groups: $CH_3$, n-$C_4H_9$, t-$C_4H_9$ or i-$C_8H_{17}$, the acyl groups such as $CH_3COO$, t-$C_4H_9COO$, the beta-ketoester group such as $CH_3C(O)CH_2C(O)O$, or a trialkylsilyl group. $R^{28}$ and $R^{29}$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl groups, for example, benzyl, phenylethyl and nonylphenyl, or the cycloalkyl groups, for example, cyclohexyl and cyclooctyl. R29 may also be hydrogen. Methyl is particularly suitable for the $R^{28}$ and $R^{29}$ groups. Each occurrence of z is 0 to 100 inclusive and each occurrence of w is 0 to 100 inclusive. In one embodiment, the values of z and w are 1 to 50 inclusive.

As indicated above, in one embodiment the present invention provides a process for producing a silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the silylated product, wherein the catalyst is a complex of the Formula (I) or an adduct thereof. As indicated above, in one embodiment the present invention provides a process for producing a silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the silylated product, wherein the catalyst is a complex of the Formula (IV) or an adduct thereof. In one embodiment, the silylated product from the process comprises a hydrosilylated product. In one embodiment, the silylated product from the process comprises a dehydrogenative silylated product. In one embodiment, the product comprises a mixture of hydrosilylated and dehydrogenative silylated product.

The manner or order in which the respective components for carrying out the process are added to one another is not particularly limited and can be chosen as desired. In one embodiment, the silylhydride can be added to a mixture containing the metal complex and the unsaturated olefin. In another embodiment, the unsaturated olefin can be added to a mixture containing the metal complex and the silylhydride. In still another embodiment, a mixture of silylhydride and unsaturated olefin can be added to a mixture of metal complex, silylhydride and unsaturated olefin. It will be appreciated that the first mixtures in the above embodiments may be heated or preliminarily reacted prior to addition of the remaining components Effective catalyst usage for silylation ranges from 0.001 mole percent to 10 mole percent based on the molar quantity of the alkene to be reacted. Preferred levels are from 0.005 to 1 mole percent. Reaction may be run at temperatures from about −10° C. up to 300° C., depending on the thermal stability of the alkene, silyl hydride and the specific pyridine di-imine complex. Temperatures in the range, 10-100° C., have been found to be effective for most reactions. Heating of reaction mixtures can be done using conventional methods as well as with microwave devices.

The catalyst composition can be provided for either the dehydrogenative silylation or hydrosilylation reactions in an amount sufficient to provide a desired metal concentration. In one embodiment, the concentration of the catalyst is about 5% (50000 ppm) or less based on the total weight of the reaction mixture; about 1% (10000 ppm) or less; 5000 ppm or less based on the total weight of the reaction mixture; about 1000 ppm or less; about 500 ppm or less based on the total weight of the reaction mixture; about 100 ppm or less; about 50 ppm or less based on the total weight of the reaction mixture; even about 10 ppm or less based on the total weight of the reaction mixture. In one embodiment, the concentration of the catalyst is from about 10 ppm to about 50000 ppm; about 100 ppm to about 10000 ppm; about 250 ppm to about 5000 ppm; even about 500 ppm to about 2500 ppm. In one embodiment, the concentration of the metal atom is from about 100 to about 1000 ppm based on the total weight of the reaction mixture. The concentration of the metal (e.g., cobalt) can be from about 1 ppm to about 5000 ppm; from about 5 ppm to about 2500 ppm; from about 10 ppm to about 1000 ppm, even from about 25 ppm to about 500 ppm. Here as elsewhere in the specification and claims, numerical values can be combined to form new and non-disclosed ranges.

The silylation reactions of this invention can be run at subatmospheric and supra-atmospheric pressures. Typically, pressures from about 1 atmosphere (0.1 MPa) to about 200 atmospheres (20 MPa), preferably to about 50 atmospheres (5.0 MPa), are suitable. Higher pressures are effective with volatile and/or less reactive alkenes which require confinement to enable high conversions.

In one embodiment, the catalysts are useful for dehydrogenative silylation of a composition containing a silyl hydride and a compound having at least one unsaturated group. The process includes contacting the composition with a suitable metal complex, either supported or unsupported, to cause the silyl hydride to react with the compound having at least one unsaturated group to produce a dehydrogenative silylation product, which may contain the metal complex catalyst. The dehydrogenative silylation reaction can be conducted optionally in the presence of a solvent. If desired, when the dehydrogenative silylation reaction is completed, the metal complex can be removed from the reaction product by magnetic separation and/or filtration. These reactions may be performed neat, or diluted in an appropriate solvent. Typical solvents include benzene, toluene, diethyl ether, etc. It is preferred that the reaction is performed under an inert atmosphere.

Because the double bond of an alkene is preserved during the dehydrogenative silylation reaction employing these cobalt catalysts, a singly-unsaturated olefin may be used to crosslink silyl-hydride containing polymers. For example, a silyl-hydride polysiloxane, such as Momentive SL6020 Dl ($MD_{15}D^H{}_{30}M$), may be reacted with 1-octene in the presence of the cobalt catalysts of this invention to produce a crosslinked, elastomeric material. A variety of new materials can be produced by this method by varying the hydride polymer and length of the olefin used for the crosslinking. Accordingly, the catalysts used in the process of the invention have utility in the preparation of useful silicone products, including, but not limited to, coatings, for example release coatings, room temperature vulcanizates, sealants, adhesives, products for agricultural and personal care applications, and silicone surfactants for stabilizing polyurethane foams.

The cobalt complexes disclosed herein can be used as a catalyst for various reactions including, for example, the hydrosilylation of a composition containing a silyl hydride and a compound having at least one aliphatically unsaturated group. The hydrosilylation process includes contacting the composition with a cobalt complex of the Formula (I), either supported or unsupported, to cause the silyl hydride to react with the compound having at least one aliphatically unsaturated group to produce a hydrosilylation product. The hydrosilylation product may contain the components from the catalyst composition. The hydrosilylation reaction can be conducted optionally in the presence of a solvent, at subatmospheric or supra-atmospheric pressures and in batch or continuous processes. The hydrosilylation reaction can be conducted at temperatures of from about −10° C. to about 200° C. If desired, when the hydrosilylation reaction is completed, the catalyst composition can be removed from the reaction product by filtration.

It will be appreciated that the reaction of a silyl hydride with an unsaturated compound can provide a mixture of hydrosilylated and dehydrogenatively silylated products. In one embodiment, a majority of the products is the hydrosilylated product.

The cobalt complexes of the invention are, in embodiments, efficient and selective in catalyzing hydrosilylation reactions. For example, when the metal complexes of the invention are employed in the hydrosilylation of a silyl hydride and a compound containing an unsaturated group, the reaction products are essentially free of unreacted unsaturated compound and/or any dehydrogenative silylated products. In one embodiment, the reaction products do not contain the unreacted and its isomerization products. As used herein, "essentially free" is meant no more than 10 wt. %, no more than 5 wt. %, no more than 3 wt. %; even no more than 1 wt. % based on the total weight of the hydrosilylation product. "Essentially free of internal addition products" is meant that silicon is added to the terminal carbon.

Hydrosilylation and dehydrogenative silylation reactions are conducted on large scales to produce various organic and inorganic materials, including additives to household items and release coatings. The disclosed approach can see immediate commercial application for these processes, which offers a cheaper yet competitive alternative to the current precious-metal-based practices. More importantly, the present reactions provide higher selectivity and fewer by-products for certain substrates compared to existing processes.

The following examples are intended to illustrate, but in no way limit the scope of the present invention. All parts and percentages are by weight and all temperatures are in degrees Celsius unless explicitly stated otherwise. All the publications and the U.S. patents referred to in the application are hereby incorporated by reference in their entireties.

EXAMPLES

General Considerations

All air- and moisture-sensitive manipulations were carried out using standard Schlenk techniques or in an MBraun inert atmosphere dry box containing an atmosphere of purified nitrogen. Solvents for air- and moisture-sensitive manipulations were dried and deoxygenated by passing through solvent system columns and stored with 4 Å molecular sieves in the dry box. Benzene-$d_6$ was purchased from Cambridge Isotope Laboratories, dried over sodium and stored with 4 Å molecular sieves in the dry box. The 2,2';6'2"-terpyridine (terpy) ligand was obtained from Strem, dried under high vacuum overnight and brought into the dry box. Liquid substrates were dried over $LiAlH_4$ or $CaH_2$ and degassed under high vacuum before use.

NMR spectra were acquired on a Varian INOVA-500 or Bruker-500 MHz spectrometer. The chemical shifts (δ) of $^1H$ NMR spectra are given in parts per million and referenced to the solvent residual of benzene-$d_6$ (7.16 ppm).

In the equations depicting the hydrosilylation and dehydrogenative silylation reactions in Examples 13-16, the abbreviation "[Si]" is used in the formulae of the products to show the attachment of the reactive silicon atom to the unsaturated substrate. The remaining groups on the silicon atom are omitted for clarity. However, the specific reaction products formed are identified in the examples.

Example 1

Synthesis of Alloxydiphenylsilane

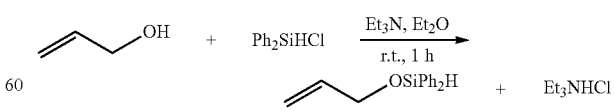

The synthesis of alloxydiphenylsilane follows a modified literature procedure as described by Bergens, S. H.; Noheda, P.; Whelan, J.; Bosnich, B. *J. Am. Chem. Soc.* 1992, 114, 2121-2128 and was carried out in air. A solution of allyl alcohol (2.9 g, 50 mmol) and triethylamine (5.1 g, 50 mmol)

in Et$_2$O (250 mL) was cooled in an ice bath. With rapid stirring, chlorodiphenylsilane (11 g, 50 mmol) was added dropwise to the solution. Large quantities of a fluffy white precipitate (Et$_3$NHCl) were observed immediately. The mixture was warmed to room temperature and stirred for 1 h. The resulting solution was filtered through Celite and washed with Et$_2$O. The filtrate was concentrated and yielded a colorless oil, which upon distillation (84-85° C., 65 mm Torr) afforded the desired product as a colorless oil in 80% yield. $^1$H NMR (400 MHz, benzene-d$_6$) δ 7.74-7.62 (m, 4H), 7.27-7.06 (m, 6H), 5.81 (ddt, J=17.1, 10.6, 4.6 Hz, 1H), 5.69 (s, 1H), 5.31 (dq, J=17.1, 1.8 Hz, 1H), 5.00 (dq, J=10.6, 1.8 Hz, 1H), 4.16 (dt, J=4.6, 1.8 Hz, 2H). $^{13}$C NMR (126 MHz, C$_6$D$_6$) δ 136.73, 135.11, 134.31, 130.66, 128.39, 128.25, 128.06, 127.87, 114.77, 65.60.

Example 2

Synthesis of Alloxydimethylsilane

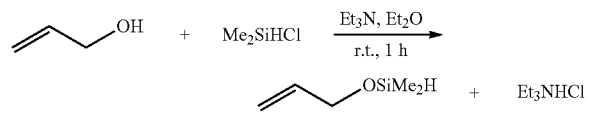

Alloxydimethylsilane was prepared in a manner similar to alloxydiphenylsilane. A solution of allyl alcohol (2.9 g, 50 mmol) and triethylamine (5.1 g, 50 mmol) in Et$_2$O (250 mL) was cooled in an ice bath. While rapid stirring, the solution was added with chlorodimethylsilane (4.7 g, 50 mmol) dropwise. Large quantities of a fluffy white precipitate (Et$_3$NHCl) were observed immediately. The mixture was warmed to room temperature and stirred for 1 hour. The resulting solution was filtered through Celite and washed with Et$_2$O. The filtrate was concentrated to yield a colorless oil, which following factional distillation (79-83° C.), afforded the product as a colorless oil in 50% yield. $^1$H NMR (400 MHz, chloroform-d) δ 5.93 (ddt, J=17.2, 10.1, 5.0 Hz, 1H), 5.26 (dq, J=17.2, 1.8 Hz, 1H), 5.12 (dq, J=10.4, 1.6 Hz, 1H), 4.68-4.55 (m, 1H), 4.18 (dt, J=5.0, 1.7 Hz, 2H), 0.23 (s, 3H), 0.23 (s, 3H).

Example 3

Synthesis of (terpy)Co(CH$_2$TMS)

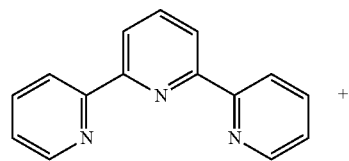

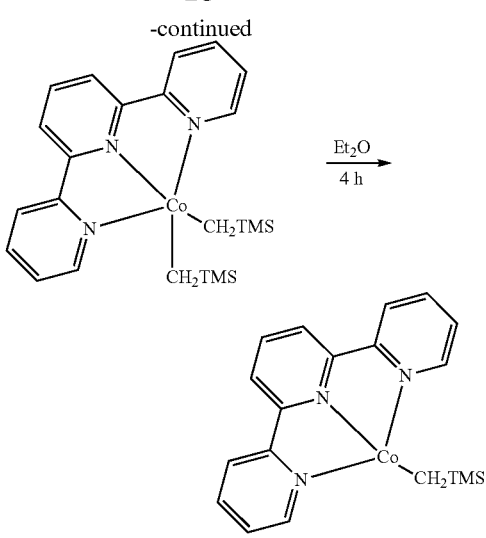

The solution of py$_2$Co(CH$_2$TMS)$_2$ (390 mg, 1 mmol) in pentane (20 mL) was prepared following literature procedures and cooled to −35° C. Zhu, D.; Janssen, F. F. B. J.; Budzelaar, P. H. M. *Organometallics* 2010, 29, 1897. The terpyridine ligand (233 mg, 1 equiv) was dissolved in pentane and added into the solution containing the cobalt compound. An immediate color change from green into purple was observed. The solution was stirred at room temperature for 0.5 hours, followed by removal of the volatile components in vacuo. The residue was dissolved in pentane and filtered through Celite to yield (terpy)Co(CH$_2$TMS)$_2$. The solution of (terpy)Co(CH$_2$TMS)$_2$ in Et$_2$O was stirred for 4 hours to generate the mono-neosilyl complex and following recrystallization from toluene/pentane at −35° C. yielded a purple solid. $^1$H NMR (400 MHz, benzene-d$_6$) δ 12.23 (d, J=6.2 Hz, 3H), 8.64 (t, J=7.6 Hz, 2H), 8.01 (t, J=6.8 Hz, 2H), 7.55 (d, J=8.2 Hz, 2H), 7.02 (d, J=7.5 Hz, 3H), 1.15 (s, 2H), −0.13 (d, J=5.0 Hz, 9H).

Example 4

Synthesis of (terpy)Co(Ph$_2$SiOC$_3$H$_5$)

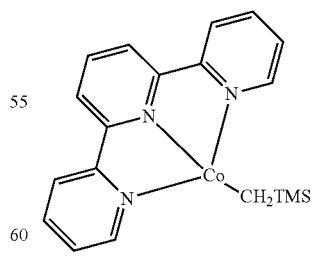

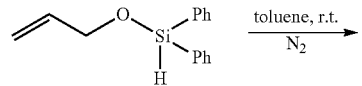

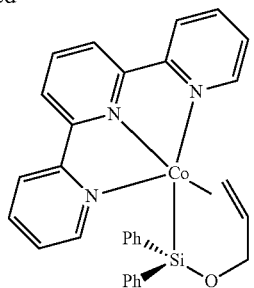

In a glove box, to a purple solution of (terpy)Co(CH₂TMS) (38 mg, 0.1 mmol) in toluene was treated with alloxydiphenylsilane (24 mg, 0.1 mmol) and stirred for 4 hours. A purple solution was observed following the addition. The solution was filtered through Celite and concentrated under vacuum. The resulting solution was layered with pentane and stored at −35° C. for 2 days and yielded purple crystals identified as the desired product. $^1$H NMR (300 MHz, benzene-d6) δ 7.85 (dd, J=7.7, 1.0 Hz, 1H), 7.75-7.57 (m, 3H), 7.34-6.74 (m, 11H), 6.67-6.60 (m, 3H), 6.54-6.43 (m, 2H), 6.36 (td, J=6.7, 1.5 Hz, 1H), 6.25 (td, J=6.5, 1.2 Hz, 1H), 5.47 (dd, J=10.2, 6.8 Hz, 1H) (s, 1H), 4.43 (t, J=9.2 Hz, 1H), 3.95-4.12 (m, 1H) 3.24-3.12 (m, 1H), 2.77 (d, J=12.5 Hz, 1H). 13C NMR (126 MHz, C6D6) δ 149.65, 148.17, 147.88, 145.19, 144.92, 144.51, 143.10, 139.71, 132.46, 132.11, 129.33, 128.0, 127.8, 127.6, 127.14, 126.68, 125.94, 125.54, 119.82, 119.62, 119.40, 119.01, 118.99, 117.81, 115.69, 74.94, 68.85, 56.32.

Example 5

Synthesis of (terpy)Co(Me₂SiOC₃H₅)

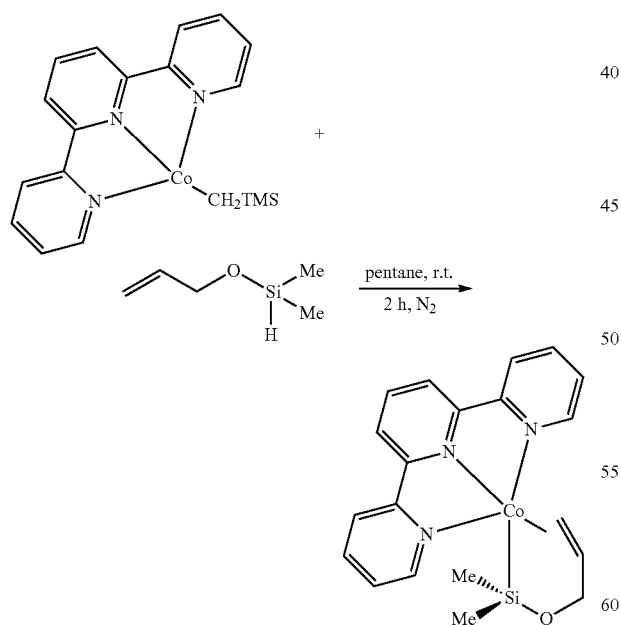

This compound was prepared in a manner similar to (terpy)Co(Ph₂SiOC₃H₅). In a glove box, to a purple solution of (terpy)Co(CH₂TMS) (38 mg, 0.1 mmol) in pentane (1 mL) was treated with alloxydimethylsilane (16 mg, 0.12 mmol) and stirred for 6 hours. A purple solution and precipitate formation were observed. The solid was isolated through filtration and purified by dissolving in toluene and passing through Celite. The resulting solution was layered with pentane and stored at −35° C. for 1 day and yielded purple crystals identified as the desired product. $^1$H NMR (300 MHz, benzene-d₆) δ 7.97 (dd, J=8.0, 0.9 Hz, 1H), 7.86 (dd, J=7.8, 0.9 Hz, 1H) 7.75 (d, J=8.2 Hz, 1H), 7.68 (d, J=6.6 Hz, 1H), 7.64 (d, J=8.3, 1H), 7.25 (t, J=7.6 Hz, 2H), 7.02 (d, J=6.4 Hz, 1H), 6.93-6.75 (m, 2H), 5.27 (dd, J=10.5, 6.2 Hz, 1H), 4.25 (t, J=10.4 Hz, 1H), 3.89-3.72 (m, 1H), 3.39 (dd, J=9.2, 2.0 Hz, 1H), 2.96 (dd, J=12.4, 1.9 Hz, 1H), −0.37 (s, 3H), −1.11 (s, 3H).

General Procedure for Catalyst Screening of the Silylation of 1-Octene with Triethoxysilane In a glove box, 1-octene (112 mg, 1 mmol) and triethoxysilane (164 mg, 1 mmol) were charged into a vial equipped with a stir bar. The solid cobalt precursor (2-3 mg, 0.5 mol %) was charged into a separate vial and then added to the vial containing substrates. The vial was sealed with a cap and stirred. After 1 hour, the reaction was quenched by exposure to air. The product mixture was analyzed by GC prior to filtration. Subsequently, it was filtered through a plug of silica gel (Fluka®, high-purity grade, pore size 60 Å, 40-63 μm particle size) typically used for flash chromatography. The resulting eluate was stripped under vacuum and analyzed by $^1$H and $^{13}$C NMR spectroscopy. The yields are based on conversion of 1-octene.

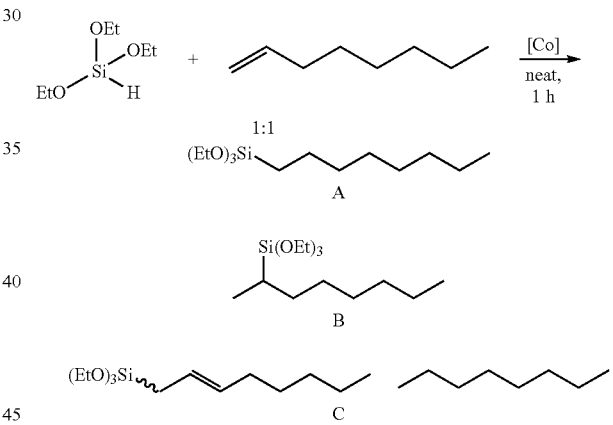

The reaction products are identified in the equation above. n-Octyltriethoxysilane, (Product A), is the anti-Markovnikov hydrosilylation product. 2-Triethoxysilyloctane, (Product B), is the Markovnikov hydrosilylation product. Product C is the allylic silane (2-Octenyltriethoxysilane) produced via dehydrogenative silylation. Octane was formed in equimolar amounts with Product C.

Example 6

Hydrosilylation of 1-Octene with Triethoxysilane Using (Terpy)Co(Ph₂SiOC₃H₅) in the Glove Box

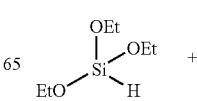

-continued

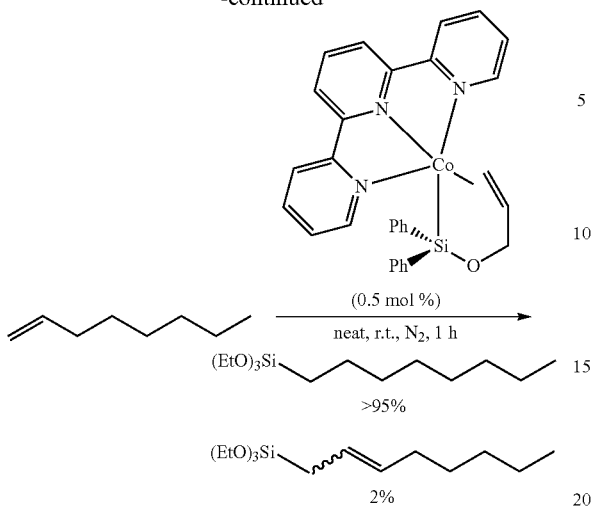

In a glove box, 1-octene (112 mg, 1 mmol) and triethoxysilane (164 mg, 1 mmol) were weighed into a vial equipped with a stir bar. Purple (terpy)Co(Ph$_2$SiOC$_3$H$_5$) (2 mg, 0.5 mol %) was weighed into a separate vial, and was subsequently combined with the substrates. The vial was stirred at ambient temperature for 1 hour. The reaction was quenched by exposure to air. The product mixture was processed as detailed in the general procedure above. GC and $^1$H NMR spectroscopy showed >95% yield of anti-Markovnikov hydrosilylation product and about 2% of the dehydrogenative silylation product.

Example 7

Hydrosilylation of 1-Octene with Triethoxysilane Using (Terpy)Co(Me$_2$SiOC$_3$H$_5$) in the Glove Box

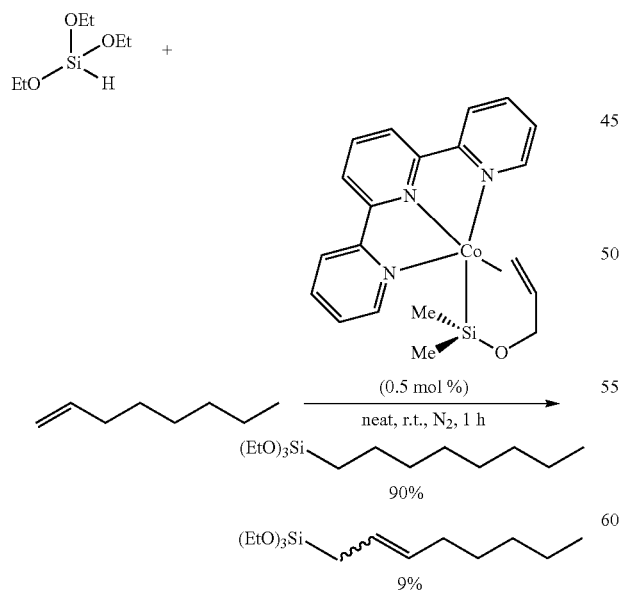

In a glove box, 1-octene (112 mg, 1 mmol) and triethoxysilane (164 mg, 1 mmol) were weighed into a vial equipped with a stir bar. Purple (terpy)Co(Me$_2$SiOC$_3$H$_5$) (2 mg, 0.5 mol %) was weighed into a separate vial, and was subsequently combined with the substrates. The contents of the vial were stirred at room temperature for 1 hour. The reaction was quenched by exposure to air. The reaction was quenched by exposure to air. The product mixture was processed as detailed in the general procedure above. GC and $^1$H NMR spectroscopy showed 90% yield of anti-Markovnikov hydrosilylation product and 9% dehydrogenative silylation product.

Example 8

Bench-Top Hydrosilylation of 1-Octene with Triethoxysilane Using (terpy)Co(Ph$_2$SiOC$_3$H$_5$) under Ar

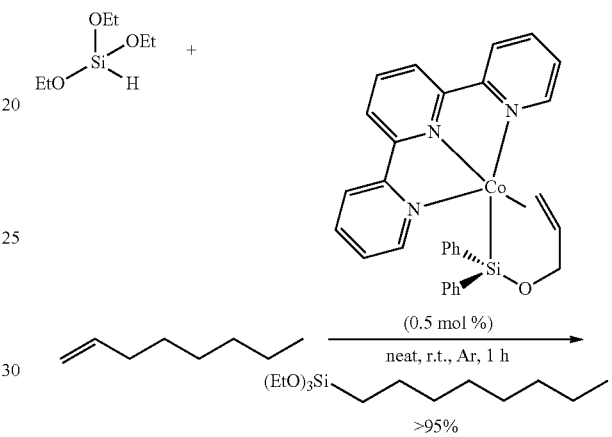

A 50 mL Schlenk flask equipped with a stir bar was charged with 1-octene (112 mg, 1 mmol) and triethoxysilane (164 mg, 1 mmol) in the glove box. The flask was sealed with a glass stopper and transferred out of the box. (terpy)Co(Ph$_2$SiOC$_3$H$_5$) (2 mg, 0.5 mol %) was charged into a vial, brought out of the box and exposed to air for 10 minutes. The solid catalyst was added into the Schlenk flask under an Ar counterflow. The flask was sealed with a glass stopper and stirred for 1 hour. The reaction was quenched by exposure to air. The reaction mixture was analyzed by GC and $^1$H NMR spectroscopy, which established >98% yield of anti-Markovnikov hydrosilylation product and trace dehydrogenative silylation product.

Examples 9 and 10

Siloxane Cross-Linking Using (Terpy)Co(Ph$_2$SiOC$_3$H$_5$) and (Terpy)Co(Me$_2$SiOC$_3$H$_5$) in the Glove Box Under N$_2$

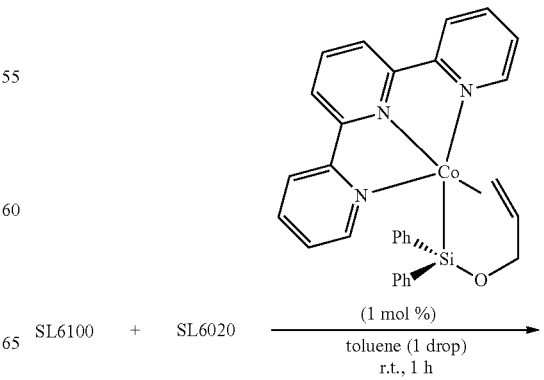

-continued

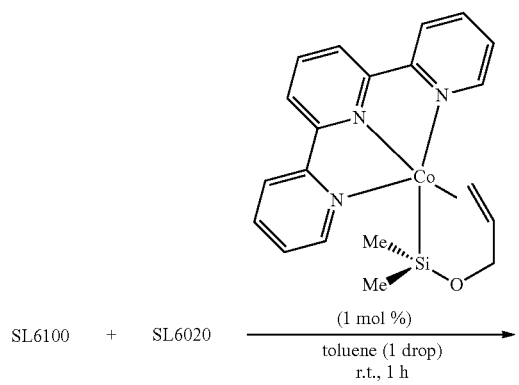

SL6100 + SL6020 →(1 mol %) toluene (1 drop) r.t., 1 h→ cross-linked silicone

All operations were done in a nitrogen filled glove box. For each example, Momentive SL6100 (1 g) and Momentive SL6020 Dl (44 mg) were weighed into a vial equipped with a stir bar. The purple solid, (terpy)Co(Ph$_2$SiOC$_3$H$_5$) (5 mg, 1 mol %) (Example 9) or (terpy)Co(Me$_2$SiOC$_3$H$_5$) (4 mg, 1 mol %) (Example 10), was weighed into a separate vial, and was subsequently combined with the substrates. During 1 h, formation of gel was observed in both vials.

Example 11

Preparation of (4-NMe$_2$-Ph-Terpy)CoCH$_2$TMS

In a nitrogen filled glove box, a scintillation vial was charged with a suspension of 0.154 g (0.319 mmol) (4-NMe$_2$-Ph-Terpy)CoCl$_2$ in approximately 10 mL of diethyl ether. The mixture was chilled at –35° C. for 10 minutes. With vigorous stirring, a diethyl ether solution of (trimethylsilyl)methyllithium (0.060 g, 0.639 mmol in 2 mL diethyl ether) was added dropwise to the chilled suspension.

During the addition, a color change to dark purple was observed. The mixture was stirred at 23° C. for 12 hours, after which it was filtered through Celite and dried in vacuo. The mixture was extracted with approximately 10 mL benzene, filtered and subsequently dried in vacuo to yield a fine dark purple solid identified as (4-NMe$_2$-Ph-Terpy)CoCH$_2$TMS. $^1$H NMR (benzene-d6, 23° C.): δ=12.29 (d, 6 Hz, 2H), 8.68 (t, 8 Hz, 2H), 8.02 (t, 7 Hz, 2H), 7.93 (d, 8 Hz, 2H), 7.52 (m, 4H), 6.59 (d, 9 Hz, 2H), 2.45 (s, 6H), –0.08 (s, 9H), one signal missing (not detected).

Example 12

Silylation of 1-octene with MD$^H$M Using (4-NMe$_2$-Ph-terpy)CoNs

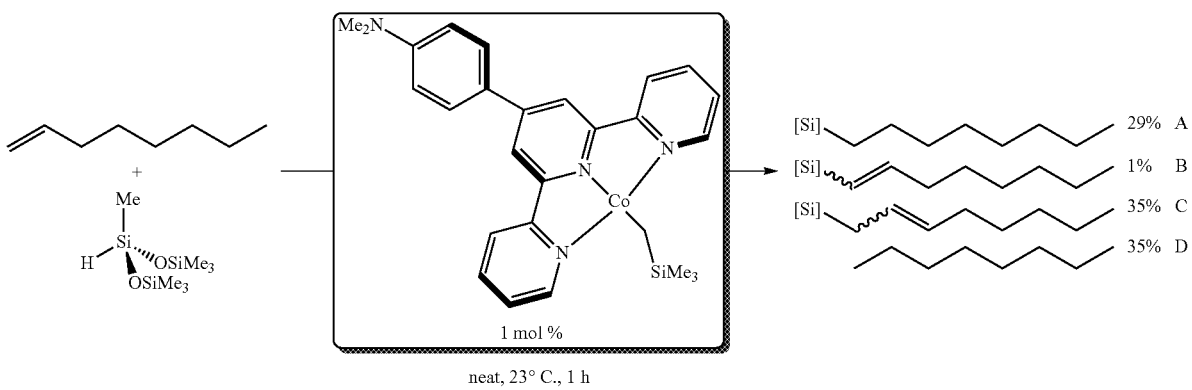

In a nitrogen-filled drybox, a scintillation vial was charged with 0.100 g (0.891 mmol) of 1-octene and approximately 0.005 g (0.009 mmol) (4-NMe$_2$-Ph-terpy)CoNs (1 mol %). MD$^H$M (0.198 g, 0.891 mmol) was then added to the mixture and the reaction was stirred at room temperature for 1 hour, after which the mixture was quenched by exposure to air. The product mixture was filtered through silica gel and eluted with hexane. The crude product mixture was analyzed by GC. Volatiles were then removed from the crude mixture product and the resulting mixture was analyzed by $^1$H and $^{13}$C NMR spectroscopy.

The results showed 29% anti-Markovnikov hydrosilylation product (A), 36% total dehydrogenative silylation products (B and C) and 35% octane (D). Note that two dehydrogenative silylation products were produced, one with vinyl unsaturated (B) and the other with allyl unsaturation (C).

Example 13

Procedure for Dehydrogenative Hydrosilylation of 1-Octene with Et$_3$SiH

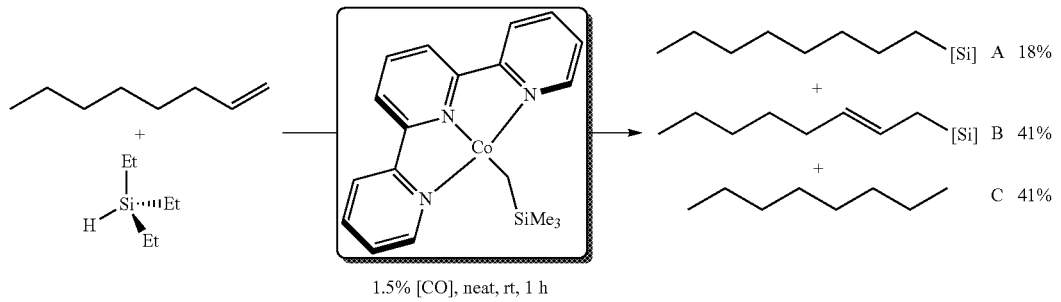

In a nitrogen filled glove box, a scintillation vial was charged with a stir bar, 0.112 g (1 mmol) of 1-octene and 0.116 g (1 mmol) of triethylsilane. (Terpy)CoCH$_2$TMS (0.002 g, 0.5 mol %) was then added into the reaction mixture as a solid. The vial was sealed with a cap and stirred at 23° C. for 1 hour, after which the reaction was quenched by exposure to air. The product mixture was filtered through silica gel and eluted with hexane. The resulting solution was dried under vacuum and analyzed by GC, $^1$H and $^{13}$C NMR spectroscopy. The yields are based on conversion of 1-octene. The yield of the hydrosilylation product (A), octyltriethylsilane, was 18% and that of the allylic dehydrogenative silylation product (B), 2-octenyltriethylsilane, was 41%. Note that an equimolar amount of the hydrogenated product (C), octane, was also formed.

Example 14

Silylation of 1-octene with 1-(2-trimethylsilylethyl)-1,1,3,3,-tetramethyldisiloxane (($CH_3$)$_3$SiC$_2$H$_4$Si($CH_3$)$_2$OSi($CH_3$)$_2$H) using (Terpy)CoCH$_2$TMS In a nitrogen-filled drybox, a scintillation vial was charged with 0.050 g (0.446 mmol) of 1-octene and approximately 0.001 g (0.004 mmol) (Terpy)CoCH$_2$TMS (1 mol %). 1-(2-trimethylsilylethyl)-1,1,3,3,-tetramethyldisiloxane (CAS Number 154455-22-8) (0.117 g, 0.446 mmol) was then added to the mixture and the reaction was stirred at room temperature for 1 hour, after which the mixture was quenched by exposure to air. The crude product mixture was analyzed by GC. It was then filtered through silica gel and eluted with hexane. Volatiles were then removed and the resulting concentrate was analyzed by $^1$H and $^{13}$C NMR spectroscopy.

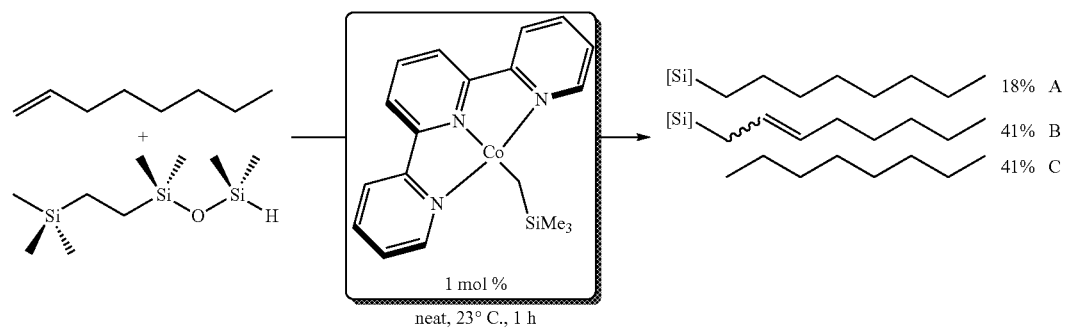

The hydrosilylation product (A), (CH$_3$)$_3$SiC$_2$H$_4$Si(CH$_3$)$_2$OSi(CH$_3$)$_2$C$_8$H$_{17}$, was obtained in 18% yield, while the dehydrogenative silylation product (B), (CH$_3$)$_3$SiC$_2$H$_4$Si(CH$_3$)$_2$OSi(CH$_3$)$_2$C$_8$H$_{15}$, and the hydrogenated product (C), octane, were formed in equimolar amounts, 41%.

Example 15

Silylation of 1-octene with (2-Trimethylsilyl)ethyldimethylsilane, (CH$_3$)$_3$SiC$_2$H$_4$Si(CH$_3$)$_2$H, using Terpy CoCH$_2$TMS In a nitrogen-filled drybox, a scintillation vial was charged with 0.050 g (0.446 mmol) of 1-octene and approximately 0.001 g (0.004 mmol) Terpy CoCH$_2$TMS (1 mol %). (2-Trimethylsilyl)ethyldimethylsilane (CAS Number 6231-75-0), (0.072 g, 0.446 mmol) was then added to the mixture and the reaction was stirred at room temperature for 1 hour, after which the mixture was quenched by exposure to air. The product mixture was filtered through silica gel and eluted with hexane. The crude product mixture was analyzed by GC. Volatiles were then removed from the crude product mixture and the residue was analyzed by $^1$H and $^{13}$C NMR spectroscopy.

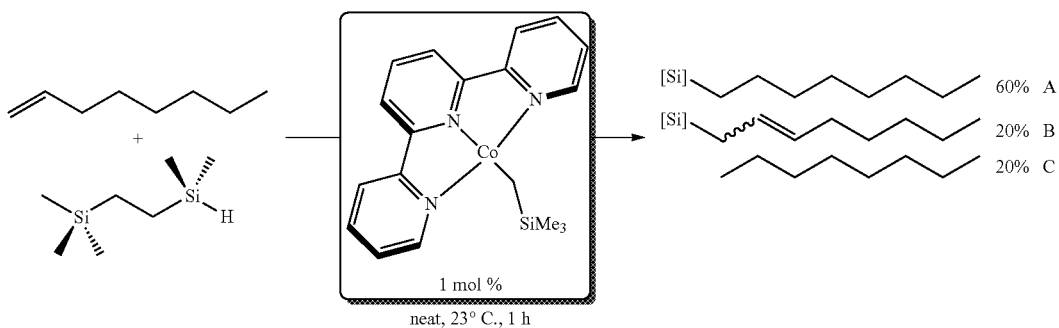

The anti-Markovnikov product, 1-(octyldimethylsilyl), 2-(trimethylsilyl)ethane, (A), was obtained in 60% yield, and the allylic dehydrogenative silylation product (B), 1-(2-octenyldimethylsilyl), 2-(trimethylsilyl)ethane in 20% yield, along with an equimolar quantity of octane.

Examples 16-20

Silylation of Vinylcyclohexene oxide (3-vinyl-7-oxabicyclo[4.1.0]heptane) with $MD^HM$ with various Terpy CoNs Catalysts These examples illustrate the use of various Terpy CoNs catalysts for the simultaneous hydrosilylation and dehydrogenative silylation of vinylcyclohexene oxide (VCHO). The catalysts differ in the substitution at the 4-position of the terpyridine ligand. Thus, in Example 16, the unsubstituted ligand was used, in Example 17, the 4-fluorophenyl, in Example 18, the 4-dimethylaminophenyl, in Example 19, the 4-mesityl and in Example 20, the 4-(pyrrolidin-1-yl).

All reactions were conducted in a nitrogen-filled drybox. In each case, a scintillation vial was charged with 0.112 g (0.899 mmol) of 3-vinyl-7-oxabicyclo[4.1.0]heptane (mixture of isomers) and (0.005 mmol, 1 mol %) of the desired modified terpy CoNs catalysts (see Table 1 below for structures). $MD^HM$ (0.100 g, 0.449 mmol) was then added to the mixture and the reaction was stirred at 23° C. for 2 minutes. The product mixture was quenched by exposure to air. It was filtered through a plug of silica gel (Fluka®, high-purity grade, pore size 60 Å, 40-63 μm particle size, typically used for flash chromatography) and eluted with hexane. The resulting solution was stripped under vacuum and was analyzed by GC, $^1H$ and $^{13}C$ NMR spectroscopy. The yields are based on conversion of 3-vinyl-7-oxabicyclo[4.1.0]heptane.

The four products shown in the equation above were identified in the reaction mixture. Product (a) is the result of dehydrogenative silylation, while (b) is the hydrosilylation product. The reduced and isomerized by-products of VCHO are (c) and (d), respectively. Table 1 shows that equimolar amounts of the dehydrogenatively silylated product (a) and hydrogenated VCHO (b) were obtained. In general, dehydrogenative silylation product (a) exceeded the hydrosilylation product (b).

TABLE 1

VCHO Conversion and Product Formation in Examples 16-20.

| EXAMPLE | R | Conversion, % | a, % | b, % | c, % | d, % |
|---|---|---|---|---|---|---|
| 16 | H | 95 | 41 | 17 | 41 | <1 |
| 17 | F–C₆H₄– | 74 | 35 | 3 | 35 | <1 |
| 18 | Me₂N–C₆H₄– | 70 | 32 | 5 | 32 | <1 |
| 19 | mesityl | 92 | 43 | 5 | 43 | <1 |

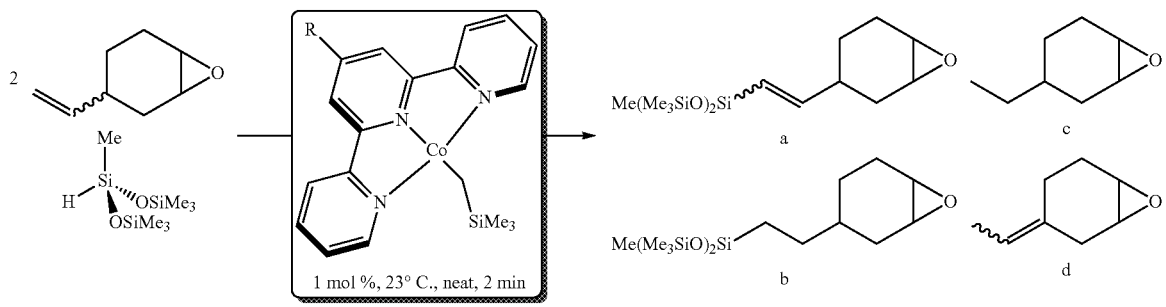

TABLE 1-continued

VCHO Conversion and Product Formation in Examples 16-20.

| EXAMPLE | R | Conversion, % | a, % | b, % | c, % | d, % |
|---|---|---|---|---|---|---|
| 20 | 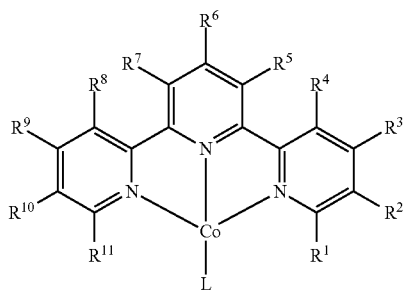 | 78 | 35 | 7 | 35 | <1 |

While, due to air and moisture intolerance of the cobalt catalysts, these catalyzed processes should be performed under air and moisture free conditions, it has now been illustrated that employment of a silyl-olefin protecting group to stabilize the cobalt catalysts yields air-stable cobalt catalysts for hydrosilylation and dehydrogenative silylation.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A complex of the Formula:

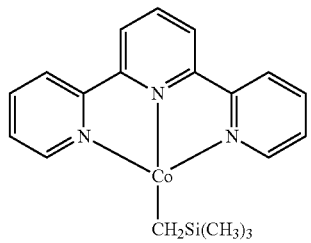

wherein each occurrence of $R^1$-$R^{11}$ is independently hydrogen, a C1-C18 alkyl, a C1-C18 substituted alkyl, a C5-C18 cycloalkyl, a C5-C18 substituted cycloalkyl, a C6-C18 aryl, a substituted C6-C18 aryl, or an inert substituent wherein one or more of $R^1$-$R^{11}$, other than hydrogen, optionally contain at least one heteroatom; optionally any two of $R^1$-$R^{11}$ vicinal to one another, $R^4$-$R^5$, and/or $R^7$-$R^8$ taken together may form a ring being a substituted or unsubstituted, saturated, or unsaturated cyclic structure; and L is —C($R^{22}$)$_2$—Si($R^{23}$)$_3$ where $R^{22}$ and $R^{23}$ are independently hydrogen, a C1-C18 alkyl, a C1-C18 substituted alkyl, a C6-C18 aryl, a substituted C6-C18 aryl, or an inert substituent, and $R^{22}$ and $R^{23}$ optionally contain at least one heteroatom.

2. The complex of claim 1, wherein $R^1$-$R^{11}$ are hydrogen.

3. The complex of claim 1, wherein the catalyst is of the formula:

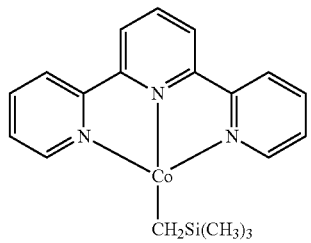

4. The complex of claim 1, wherein at least one of $R^1$-$R^{11}$ is chosen from an aryl group or a substituted aryl group.

5. The complex of claim 4, wherein the substituted aryl group is chosen from tolyl, xylyl, naphthyl, mesityl, aniline, fluorophenyl, or a combination of two or more thereof.

6. The complex of claim 1, wherein $R^1$-$R^5$ and $R^7$-$R^{11}$ are hydrogen, and $R^6$ is chosen from pyrrolidino, flourophenyl, aniline, or mesityl.

7. The complex of claim 1, wherein the complex is of the formula:

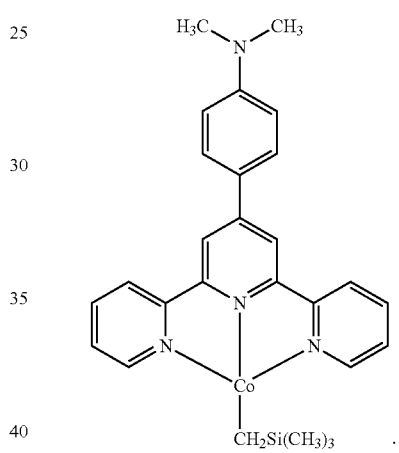

8. A process for producing a silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the silylated product, wherein the catalyst is a complex of the Formula (IV) or an adduct thereof:

(IV)

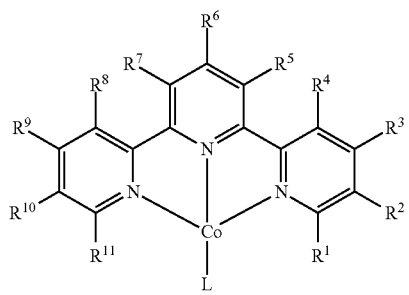

wherein each occurrence of $R^1$-$R^{11}$ is independently hydrogen, a C1-C18 alkyl, a C1-C18 substituted alkyl, a C5-C18 cycloalkyl, a C5-C18 substituted cycloalkyl, a C6-C18 aryl, a substituted C6-C18 aryl, or an inert substituent wherein one or more of $R^1$-$R^{11}$, other than hydrogen, optionally contain at least one heteroatom; optionally any two of $R^1$-$R^{11}$ vicinal to one another, $R^4$-$R^5$, and/or $R^7$-$R^8$ taken together may form a ring being a substituted or unsubstituted, saturated, or unsaturated cyclic structure; and L is chosen from hydrogen, a C1-C18 alkyl, C1-C18 substituted alkyl, a C6-C18 aryl, a substituted C6-C18 aryl group, an alkaryl group, or an aralkyl group, an alkyl trialkylsilyl, where L optionally contains at least one heteroatom.

9. The process of claim 8, wherein $R^1$-$R^{11}$ are hydrogen.

10. The process of claim 8, wherein L is —C($R^{22}$)$_2$—Si($R^{23}$)$_3$ where $R^{22}$ and $R^{23}$ are independently hydrogen, a C1-C18 alkyl, a C1-C18 substituted alkyl, a C6-C18 aryl, a substituted C6-C18 aryl, or an inert substituent, and $R^{22}$ and $R^{23}$ optionally contain at least one heteroatom.

11. The process of claim 10, wherein $R^1$-$R^{11}$ are hydrogen.

12. The process of claim 8, wherein the catalyst is of the formula:

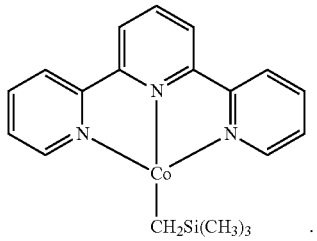

13. The process of claim 8, wherein at least one of $R^1$-$R^{11}$ is chosen from an aryl group or a substituted aryl group.

14. The process of claim 13, wherein the substituted aryl group is aniline.

15. The process of claim 8, wherein the complex is of the formula:

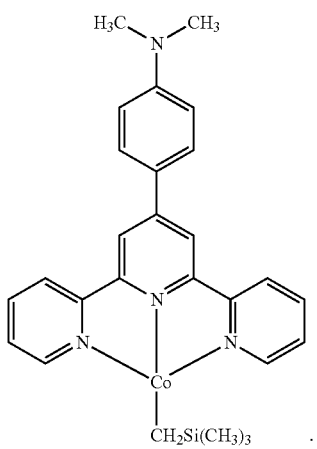

16. The process of claim 8, further comprising removing the complex and/or derivatives thereof from the silylated product.

17. The process of claim 8, wherein the silylated product comprises a hydrosilylation product.

18. The process of claim 8, wherein the silylated product comprises a dehydrogenatively silylated product.

19. The process of claim 8, wherein the silylated product comprises a mixture of (i) a hydrosilylation product, and (ii) a dehydrogenative silylated product.

20. The process of claim 8, wherein the unsaturated compound (a) is chosen from a linear or branched olefin; a cycloalkene; an alkyl-capped allyl polyether; a vinyl-functional alkyl-capped allyl or methallyl polyether; an alkyl-capped terminally unsaturated amine; an alkyne; a terminally unsaturated acrylate or methacrylate; an unsaturated aryl ether; a vinyl-functionalized polymer or oligomer; a vinyl-functionalized and/or terminally-unsaturated alkenyl-functional silane; and/or silicone; an unsaturated fatty acid; an unsaturated ester; or combinations of two or more thereof.

21. The process of claim 8, wherein the reaction is conducted under an inert atmosphere.

22. The process of claim 8, wherein the reaction is carried out at a temperature of
−10° C. to 300° C.

23. The process according to claim 8, wherein the silyl hydride comprises a hydride fluid chosen from one or a combination of compounds of the formulas:

$$R^{24}{}_m SiH_p X_{4-(m+p)};$$

$$M_a M^H{}_b D_c D^H{}_d T_e T^H{}_f Q_g;$$

$$R^{30}{}_3 Si(CHR^{30})_x SiOSiR^{30}{}_2(OSiR^{30}{}_2)_y OSiR^{30}{}_2 H,$$

$$R^{30}{}_3 Si(CHR^{30})_x SiR^{30}{}_2 H$$

where each $R^{24}$ is independently a substituted or unsubstituted aliphatic or aromatic hydrocarbyl group; X is halogen, alkoxy, acyloxy, or silazane; m is 0-3; p is 1-3, with the proviso that the tetravalency of silicon is preserved; M represents a monofunctional group of formula $R^{25}{}_3SiO_{1/2}$; a D represents a difunctional group of formula $R^{25}{}_2SiO_{2/2}$; a T represents a trifunctional group of formula $R^{25}SiO_{3/2}$; Q represents a tetrafunctional group of formula $SiO_{4/2}$; $M^H$ represents $HR^{25}{}_2SiO_{1/2}$, $T^H$ represents $HSiO_{3/2}$, and $D^H$ group represents $R^{25}HSiO_{2/2}$; each occurrence of $R^{25}$ is independently a $C_1$-$C_{18}$ alkyl, a $C_1$-$C_{18}$ substituted alkyl, a $C_6$-$C_{14}$ aryl or substituted aryl, wherein $R^{25}$ optionally contains at least one heteroatom; subscripts a, b, c, d, e, f, and g are such that the molar mass of the compound is between 100 and 100,000 Dalton; each occurrence of $R^{30}$ is independently a C1-C18 alkyl, a C1-C18 substituted alkyl, a C6-C14 aryl or substituted aryl; x is 1-8, and y is 0-10.

24. The process of claim 8, wherein the complex is immobilized on a support.

25. The complex of claim 24, wherein the support is chosen from carbon, silica, alumina, MgCl$_2$, zirconia, polyethylene, polypropylene, polystyrene, poly(aminostyrene), sulfonated polystyrene, or a combination of two or more thereof.

26. A composition produced by the process of claim 8, wherein the composition contains the catalyst or derivatives thereof, and comprises at least one component selected from the group of silanes, silicone fluids, and crosslinked silicones, or a combination of two or more thereof.

* * * * *